US010258670B2

(12) United States Patent
Davies et al.

(10) Patent No.: US 10,258,670 B2
(45) Date of Patent: *Apr. 16, 2019

(54) METHODS FOR TREATING NEUROLOGICAL CONDITIONS AND COMPOSITIONS AND MATERIALS THEREFOR

(71) Applicant: SCIDEC THERAPEUTICS, INC., Cambridge, MA (US)

(72) Inventors: Stephen Davies, Flemington (AU); Kenneth Hal Minor, Brighton, CO (US)

(73) Assignee: SCIDEC THERAPEUTICS, INC., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/419,116

(22) Filed: Jan. 30, 2017

(65) Prior Publication Data

US 2017/0136098 A1 May 18, 2017

Related U.S. Application Data

(63) Continuation of application No. 14/714,626, filed on May 18, 2015, now Pat. No. 9,592,276, which is a continuation of application No. 13/331,933, filed on Dec. 20, 2011, now Pat. No. 9,061,047.

(60) Provisional application No. 61/424,769, filed on Dec. 20, 2010.

(51) Int. Cl.
*A01N 37/18* (2006.01)
*A01N 61/00* (2006.01)
*A61K 38/00* (2006.01)
*A61K 31/737* (2006.01)
*A61K 38/39* (2006.01)
*A61K 45/06* (2006.01)
*A61K 9/00* (2006.01)
*A61K 38/17* (2006.01)

(52) U.S. Cl.
CPC ............ *A61K 38/39* (2013.01); *A61K 9/0085* (2013.01); *A61K 31/737* (2013.01); *A61K 38/1709* (2013.01); *A61K 45/06* (2013.01)

(58) Field of Classification Search
None
See application file for complete search history.

(56) References Cited

U.S. PATENT DOCUMENTS

| 9,061,047 | B2 | 6/2015 | Davies et al. |
| 9,592,276 | B2* | 3/2017 | Davies ................. A61K 31/737 |
| 2008/0140048 | A1 | 6/2008 | Keimel et al. |
| 2012/0157976 | A1 | 6/2012 | Davies et al. |

FOREIGN PATENT DOCUMENTS

| JP | 2010047533 A | 3/2010 |
| WO | 2003070195 A2 | 8/2003 |
| WO | 2008070769 A1 | 6/2008 |
| WO | 2010065917 A1 | 6/2010 |

OTHER PUBLICATIONS

Bruning et al. "CAR is a cell-cell adhesion protein in human cancer cells and is expressionally modulated by dexamethasone, TNF?, and TGF?," Gene Therapy, Feb. 2003, vol. 10, No. 3, pp. 198-205.
Cai et al., "Prior Exposure to Neurotrophins Blocks Inhibition of Axonal Regeneration by MAG and Myelin via a cAMP-Dependent Mechanism," Neuron, vol. 22, 1999, 89-101.
Chen et al., "Comparison of Polymer Scaffolds in Rat Spinal Cord: a Step Toward Quantitative Assessment of Combinatorial Approaches to Spinal Cord Repair," Biomaterials, vol. 32, 2011, 8077-8086.
Cigognini et al., "Evaluation of Early and Late Effects into the Acute Spinal Cord Injury of an Injectable Functionalized Self-Assembling Scaffold," PLoS ONE 6, 2011, e19782.
Csordas et al., "Sustained Down-Regulation of the Epidermal Growth Factor Receptor by Decorin. A Mechanism for Controlling Tumor Growth in Vivo," J. Biol. Chem., vol. 275, 2000, 32879-32887.
Davies et al. "Regeneration of adult axons in white matter tracts of the central nervous system," Nature, vol. 390, 1997, 680-683.
Davies et al., "Adult Axon Regeneration in Adult CNS White Matter" [letter comment], Trends Neurosci., vol. 21, 1998, 515.
Davies et al., "Astrocytes Derived From Glial Restricted Precursors Promote Spinal Cord Repair," Journal of Biology, vol. 5:7, 2006.
Davies et al., "Decorin Promotes Plasminogen/Plasmin Expression within Acute Spinal Cord Injuries and by Adult Microglia In Vitro," J Neurotrauma, vol. 23, 2006, 397-408.
Davies et al., "Decorin Suppresses Neurocan, Brevican, Phosphacan and NG2 Expression and Promotes Axon Growth Across Adult Rat Spinal Cord Injuries," Eur. J Neurosci., vol. 19, 2004, 1226-1242.
Davies et al., "Regeneration of Cut Adult Axons Fails Even in the Presence of Continuous Aligned Glial Pathways," Experimental Neurology, vol. 142, 1996, 203-216.
Davies et al., "Robust Regeneration of Adult Sensory axons in Degenerating White Matter of the Adult Rat Spinal Cord," J. Neurosci, vol. 19, 1999, 5810-5822.
De Camilli et al., "Synapsin I (Protein 1), a Nerve Terminal-Specific Phosphoprotein. II. Its Specific Association with Synaptic Vesicles Demonstrated by Immunocytochemistry in Agarose-Embedded Synaptosomes," J Cell Biol. vol. 96, May 1983, 1355-1373.
De Winter et al., Injury-Induced Class 3 Semaphorin Expression in the Rat Spinal Cord, Exp. Neurol., vol. 175, 2002, 61-75.
Dougherty et al., "Brain-Derived Neurotrophic Factor in Astrocytes, Oligodendrocytes, and Microglia/Macrophages after Spinal Cord Injury," Neurobiol. Dis., vol. 7, 2000 574-585.

(Continued)

*Primary Examiner* — Olga N Chernyshev
(74) *Attorney, Agent, or Firm* — Lando & Anastasi, LLP

(57) ABSTRACT

The present invention generally relates to methods, compositions and materials for treatment of and promotion of neurological functional recovery from neurological conditions including central nervous system injuries and/or diseases.

10 Claims, 9 Drawing Sheets

(56) References Cited

OTHER PUBLICATIONS

Edwards et al., "Processing of the Native Nerve Growth Factor Precursor to Form Biologically Active Nerve Growth Factor," J Biol. Chem., vol. 263, 1988, 6810-6815.
European Search Report from European Application Serial No. 11852038.6 dated Jul. 8, 2014.
Fan et al., "Decorin Derived Antiangiogenic Peptide LRR5 Inhibits Endothelial Cell Migration by Interfering with VEGF-Stimulated NO Release," Int. J Biochem. Cell Biol., vol. 40, 2008, 2120-2128.
Ferguson et al., "MMP-2 and MMP-9 Increase the Neurite-Promoting Potential of Schwann Cell Basal Laminae and are Upregulated in Degenerated Nerve," Mol. Cell Neurosci., vol. 16, 2000, 157-167.
Gensel et al., "Behavior and Histological Characterization of Unilateral Cervical Spinal Cord Contusion Injury in Rats," J. Neurotrauma, vol. 23, 2006, 36-54.
Guertin "A Technological Platform to Optimize Combinatorial Treatment Design and Discovery for Chronic Spinal Cord Injury," Journal of Neuroscience Research, 2008, vol. 86, pp. 3039-3051.
Gulino et al., "Synaptic Plasticity Modulates the Spontaneous Recovery of Locomotion after Spinal Cord Hemisection," Neurosci. Res., vol. 57, 2007,148-156.
Hamers et al., "CatWalk-Assisted Gait Analysis in the Assessment of Spinal Cord Injury." J. Neurotrauma, vol. 23, 2006, 537-548.
Hiebert et al., "Brain-Derived Neurotrophic Dactor Applied to the Motor Cortex Promotes Sprouting of Corticospinal Fibers but not Regeneration into a Peripheral Nerve Transplant," J. Neurosci. Res., vol. 69, 2002, 160-168.
Hocking et al. Leucine-Rich Repeat Glycoproteins of the Extracellular Matrix. Matrix Biol., vol. 17, 1998, 1-19.
International Preliminary Report on Patentability for International (PCT) Patent Application No. PCT/US2011/066199, dated Jul. 4, 2013 8 pages.
International Search Report for International (PCT) Patent Application No. PCT/US2011/066199, dated Apr. 23, 2012 3 pages.
Iozzo et al. "Small-Leucine-Rich Proteoglycans," Biology of Extracellular Matrix the Extracellular Matrix: An Overview, 2011, pp. 197-231, Abstract Only.
Iozzo, "The Biology of the Small Leucine-Rich Proteoglycans Functional Network of Interactive Proteins." J. Biol. Chern., Jul. 1999, vol. 274, No. 27, pp. 18843-18846.
Jarvinen et al., "Target-seeking Antifibrotic Compound Enhances Wound Healing and Suppresses Scar Formation in Mice," Proc. Natl. Acad. Sci. U.S.A., vol. 107, 2010, 21671-21676.
Johnson et al., Small Leucine Rich Repeat Proteoglycans (SLRPs) in the Human Sclera: Identification of Abundant Level of PRELP, Mol. Vis., vol. 12,2006, 1057-1066.
Koelsch et al., "Transgene-Mediated GDNF Expression Enhances Synaptic Connectivity and GABA Transmission to Improve Functional Outcome after Spinal Cord Contusion," J Neurochem., vol. 113, 2010, 143-152.
Lee et al., "Regulation of Cell Survival by Secreted Proneurotrophins," Science, vol. 294, 2001, 1945-1948.
Logan et al., "Decorin Attenuates Gliotic Scar Formation in the Rat Cerebral Hemisphere," Exp. Neural., vol. 159, 1999, 504-510.
Lu, B. "Expression of Synapsin I Correlates with Maturation of the Neuromuscular Synapse," Neuroscience, vol. 74, 1996, 1087-1097.
Mackay et al. "Basement Membrane Type IV Collagen Degradation: Evidence for the Involvement of a Proteolytic Cascade Independent of Metalloproteinases," Cancer Research, Sep. 1990, vol. 50, pp. 5997-6001.
Minor et al., "Decorin Promotes Robust Axon Growth on Inhibitory CSPGs and Myelin via a Direct Effect on Neurons," Neurobiol. Dis., vol. 32, 2008, 88-95.
Minor et al., "Decorin, Erythroblastic Leukaemia Viral Oncogene Homologue B4 and Signal Transducer and Activator of Transcription 3 Regulation of Semaphorin 3A in Central Nervous System Scar Tissue," Brain, 2011, vol. 134, pp. 1140-1155.
Minor et al., "Delayed treatment of spinal cord injuries with decorin promotes robust functional recovery" presented Tuesday, Nov. 15, 2011 8AM-9AM—Neuroscience Abatract viewer and itinerary planner, vol. 41, (2011)—41st Annual Meeting of the Society-For-Neuroscience; Washington, DC, USA (Abstract Only).
Minor, et al., "Decorin, erythroblastic leukaemia viral oncogene homologue B4 and signal transducer and activator of transcription 3 regulation of semaphorin 3A in central nervous system scar tissue" Brain (2010) 134:1140-1155.
Morgenstern et al., "Chondroitin Sulphate Proteoglycans in the CNS Injury Response," Prog Brain Res 137, 2002, 163-173.
Mundy et al., "Protein Biomarkers Associated with Growth and Synaptogenesis in a Cell Culture Model of Neuronal Development," Toxicology, vol. 249, 2008, 220-229.
Murphy et al., The role of Plasminogen Activators in the Regulation of Connective Tissue Metalloproteinases, Ann. N.Y. Acad. Sci., vol. 667, 1992, 1-12.
Murray et al., "Transplantation of Genetically Modified Cells Contributes to Repair and Recovery from Spinal Injury," Brain Res. Rev., vol. 40, 2002, 292-300.
Nakamura et al. , "Differences in Neurotrophic Factor Gene Expression Profiles Between Neonate and Adult Rat Spinal Cord After Injury," Exp. Neural. , vol. 169, 2001, 407-145.
Oudega et al., "Nerve Growth Factor Promotes Regeneration of Sensory Axons into Adult Rat Spinal Cord," Exp. Neural., vol. 140, 1996, 218-229.
Pang et al., "Cleavage of proBDNF by tPA/plasmin is Essential for Long-Term Hippocampal Plasticity," Science, vol. 306, 2004, 487-491.
Pasterkamp et al. "Peripheral Nerve Injury Fails to Induce Growth of Lesioned Ascending Dorsal Column Axons into Spinal Cord Scar Tissue Expressing the Axon Repellent Semaphorin3A," Eur. J. Neurosci., vol. 13, 2001 , 457-471.
Pasterkamp et al. , "Expression of the Gene Encoding the Chemorepellent Semaphorin III is Induced in the Fibroblast Component of Neural Scar Tissue Formed Following Injuries of Adult but not Neonatal CNS," Mol. Cell Neurosci, vol. 13, 1999, 143-166.
Pasterkamp et al., "Role for Semaphorin III and its Receptor Neuropilin-1 in Neuronal Regeneration and Scar Formation," Prog. Brain Res., vol. 117, 1998, 151-170).
Pasterkamp et al., "Semaphorin Junction: Making Tracks Toward Neural Connectivity," Curr. Opin. Neurobiol, vol. 13, 2003, 79-89.
Plunet eta I. "Promoting axonal regeneration in the central nervous system by enhancing the cell body response to axotomy," Journal of Neurosceince Research, Apr. 2002, vol. 68, No. 1, pp. 1-6.
Properzi et al., "Chondroitin 6-Sulphate Synthesis is Up-Regulated in Injured CNS, Induced by Injury-Related Cytokines and Enhanced in Axon-Growth Inhibitory Glia," Eur. J. Neurosci., vol. 21, 2005, 378-390.
Rabchevsky et al., "A Role for Transforming Growth Factor Alpha as an Inducer of Astrogliosis." J. Neurosci., vol. 18, 1998, 10541-10552.
Salgado et al. "Modulation of small leucine-rich proteoglycans (SLRPs) expression in the mouse uterus by estradiol and progesterone," Reproductive Biology and Endocrinology, Feb. 2011, vol. 9, 13 pages.
Santra et al., "Decorin Binds to a Narrow Region of the Epidermal Growth Factor (EGF) Receptor, Partially Overlapping but Distinct from the EGF-Binding Epitope," J. Biol. Chem., vol. 277, 2002, 35671-35681.
Schaefer et al. , "Biological Functions of Small Leucine-Rich Proteoglycans: from Genetics to Signal Transduction," J. Biol. Chem., vol. 283(31), 2008, 21305-21309.
Schmidt et al., "Interaction of the Small Proteoglycan Decorin with Fibronectin. Involvement of the Sequence NKISK of the Core Protein," Biochem, J. vol. 280 (Pt2), 1991,411-414.
Schnadelbach et al. "Expression of DSD-1-PG in primary neural and glial-derived cell line cultures, upregulation by TGF-?, and implications for cell-substrate interactions of the glial cell line Oli-neu," Glia, Jun. 1998, vol. 23, No. 2, pp. 99-199.
Schonherr et al. , "Decorin Core Protein Fragment Leu155-Val260 Interacts with TGF-Beta but Does not Compete for Decorin Binding to Type I Collagen," Arch. Biochem. Biophys., vol. 355, 1998, 241-248.

(56) References Cited

OTHER PUBLICATIONS

Schucht et al., Anatomical Correlates of Locomotor Recovery Following Dorsal and Ventral Lesions of the Rat Spinal Cord, Exp. Neural., vol. 176, 2002, 143-153.

Schwab et al., "Nogo and Axon Regeneration," Curr. Opin. Neurobiol., vol. 14, 2004, 118-124.

Stichel et al., "Basal Membrane-Depleted Scar in Lesioned CNS: Characteristics and Relationships with Regenerating Axons," Neuroscience, vol. 93, 1999, 321-333.

Stichel et al., "Differential Expression of the Small Chondroitin/Dermatan Sulfate Proteoglycans Decorin and Biglycan After Injury of the Adult Rat Brain," Brain Res., vol. 704(2), 1995, 263-274.

Sulochana et al., "Peptides Derived from Human Decorin Leucine-Rich Repeat 5 Inhibit Angiogenesis," J Biol. Chem., vol. 280, 2005, 27935-27948.

Tang et al., "Changes in Distribution, Cell Associations, and Protein Expression Levels of NG2, Neurocan, Phosphacan, Brevican, Versican V2, and Tenascin-C During Acute to Chronic Maturation of Spinal Cord Scar Tissue," J. Neurosci. Res., vol. 71, 2003, 427-444.

Thiel, G. "Synapsin I, Synapsin II, and Synaptophysin: Marker Proteins of Synaptic Vesicles," Brain Pathol., vol. 3, 1993, 87-95.

Vogel et al., "Specific Inhibition of Type I and Type II Collagen Fibrilogenesis by the Small Proteoglycan of Tendon," Biochem J, vol. 222, 1984, 587-597.

Webb et al., "Compensatory Locomotor Adjustments of Rats with Cervical or Thoracic Spinal Cord Hemisections," J. Neurotrauma, vol. 19, 2002, 239-256.

Webb et al., "Unilateral Dorsal Column and Rubrospinal Tract Injuries Affect Overground Locomotion in the Unrestrained Rat," Eur. J. Neurosci., vol. 18, 2003, 412-422.

Wong et al., "A three-month, open-label, single-arm trial evaluating the safety and pharmacokinetics of oral lithium in patients with chronic spinal cord injury," Spinal Cord, 2011, Vo. 49, pp. 94-98.

Written Opinion for International (PCT) Patent Application No. PCT/US2011/066199, dated Apr. 23, 2012 6 pages.

Wu et al., "The tissue Plasminogen Activator 5 (tPA)/Plasmin Extracellular Proteolytic System Regulates Seizure-Induced Hippocampal Mossy Fiber Outgrowth Through a Proteoglycan Substrate," J. Cell Biol., vol. 148, 2000, 1295-1304.

Yamaguchi et al., "Negative Regulation of Transforming Growth Factor-Beta by the Proteoglycan Decorin," Nature, vol. 346, 1990, 281-284.

Yiu et al. "Glial Inhibition of CNS Axon Regeneration," Nat Rev Neurosci., vol. 7, 2006, 617-627.

Zuo et al. "Neuronal Matrix Metalloproteinase-2 Degrades and Inactivates a Neurite-Inhibiting Chondroitin Sulfate Proteoglycan," The Journal of Neuroscience, Jul. 1998, vol. 18, No. 14, pp. 5203-5211.

"Traumatic brain injuries," In: Neurological Disorders: public health challenges, World Health Organization, Feb. 2007, pp. 164-175.

Andrews et al., "Alterations in Chondroitin Sulfate Proteoglycan Expression Occur Both at and Far from the Site of Spinal Contusion Injury," Exp. Neural. ePub ahead of print, 2011.

Asher et al., "Neurocan is Upregulated in Injured Brain and in Cytokine-Treated Astrocytes," J. Neurosci., vol. 20, 2000, 2427-2438.

Bregman et al., "Transplants and Neurotrophic Factors Prevent Atrophy of Mature CNS Neurons After Spinal Cord Injury," Exp. Neurol., vol. 149, 1998, 13-27.

\* cited by examiner

METHODS FOR TREATING NEUROLOGICAL CONDITIONS AND COMPOSITIONS AND MATERIALS THEREFOR

CROSS-REFERENCE TO RELATED APPLICATIONS

This application is a continuation of U.S. application Ser. No. 14/714,626 filed May 18, 2015 which claims priority to U.S. application Ser. No. 13/331,933 filed Dec. 20, 2011 which claims priority under 35 U.S.C. § 119 from U.S. provisional application Ser. No. 61/424,769 filed Dec. 20, 2010, the entire contents of which is incorporated by reference.

FIELD OF INVENTION

The present invention generally relates to methods, compositions and materials for treatment and promotion of neurological functional recovery from neurological conditions including central nervous system injuries and/or diseases.

BACKGROUND OF THE INVENTION

Neurological conditions are disorders of the body's nervous system. Structural, biochemical or electrical abnormalities in the brain, spinal cord, or in the nerves leading to or from them, can result in symptoms such as paralysis, muscle weakness, lack of coordination, loss of sensation, as well as pain. Interventions include preventative measures, lifestyle changes, physiotherapy or other therapy, neuro-rehabilitation, pain management, medication, or operations performed by neurosurgeons (WHO Neurological Disorders: Public Health Challenges, 2006). These conditions or disorders can be categorized according to the primary location affected, the primary type of dysfunction involved, or the primary type of cause. The broadest division is between central nervous system (CNS) disorders and peripheral nervous system (PNS) disorders (Merck Manual: Brain, Spinal Cord and Nerve Disorders, 2010-2011).

Traumatic injury to the adult central nervous system (CNS) is associated with multiple different types of damage, all of which pose substantial challenges to attempts to achieve tissue repair. Restoration of neurological function after severe injury requires regenerative growth of severed motor and sensory axons through the provision of growth factors, appropriate substrates and/or overriding of a variety of inhibitors that prevent axon regeneration.

Currently there is an acute clinical demand for novel therapies that promote robust levels of functional recovery when administered to the traumatically injured or diseased central nervous system (CNS). Scar tissue that forms after traumatic injury to the adult mammalian CNS is rich in axon growth inhibitory chondroitin sulfate proteoglycans (CSPGs) and inhibitory to axon growth (Davies, S. J., et al. Regeneration of adult axons in white matter tracts of the central nervous system. *Nature* 390, 680-683 (1997); Davies, S. J. et al., Robust regeneration of adult sensory axons in degenerating white matter of the adult rat spinal cord *J. Neurosci* 19, 5810-5822 (1999)). Misaligned fibrotic scar tissue in large CNS injuries clearly presents a physical barrier to axon growth, however failure of axon regeneration can even occur within minimal injuries in which tissue alignment is rapidly restored (Davies S. J., et al. Regeneration of cut axons fails even in the presence of continuous aligned glial pathways. Exp. Neurol. 142; 203-216 (1996)), highlighting a molecular inhibition of axon growth within CNS injuries. Several individual CSPGs, such as neurocan, NG2, brevican and phosphacan, have been shown to be inhibitory to axon growth in vitro and are up-regulated at sites of adult CNS injury (reviewed in Morgenstern D. A., et al., Chondroitin sulphate proteoglycans in the CNS injury response. *Prog. Brain Res* 137, 163-173 (2002)). Other axon growth inhibitors such semaphorin 3A have also been shown to be upregulated within scar tissue at sites of brain and spinal cord injury (Pasterkamp R. J. et al. Expression of the gene encoding the chemorepellent semaphorin III is induced in the fibroblast component of neural scar tissue formed following injuries of adult but not neonatal CNS, *Mol. Cell Neurosci* 13: 143-166(1999): Pasterkamp R. J. et al. Peripheral nerve injury fails to induce growth of lesioned ascending dorsal column axons into spinal cord scar tissue expressing the axon repellent Semaphorin3A, *Eur. J. Neurosci.* 13: 457-471(2001): Pasterkamp R. J. and. Kolodkin A. L, Semaphorin junction: making tracks toward neural connectivity, *Curr. Opin. Neurobiol.* 13:79-89 (2003)). In addition to upregulation of inhibitory CSPGs within scar tissue that forms directly at sites of injury, inhibitory CSPGs and semaphorin 3A are also known to be present at high levels with normal spinal cord gray matter and after CNS injury (Pasterkamp R. J. et al. Expression of the gene encoding the chemorepellent semaphorin III is induced in the fibroblast component of neural scar tissue formed following injuries of adult but not neonatal CNS, *Mol. Cell Neurosci* 13: 143-166(1999); Pasterkamp R. J. and. Kolodkin A. L, Semaphorin junction: making tracks toward neural connectivity, *Curr. Opin. Neurobiol.* 13:79-89 (2003); Andrews E. M. et al. Alterations in chondroitin sulfate proteoglycan expression occur both at and far from the site of spinal contusion injury, *Exp. Neurol.* ePub ahead of print (2011); Tang X., et al. Changes in distribution, cell associations, and protein expression levels of NG2, neurocan, phosphacan, brevican, versican V2, and tenascin-C during acute to chronic maturation of spinal cord scar tissue, *J. Neurosci. Res.* 71: 427-444(2003). Furthermore, it has been shown that myelin sheaths around axons with adult CNS white matter also presents a variety of axon growth inhibitory molecules such as NOGO (Neurite outgrowth inhibitor), myelin associated glycoprotein (MAG) and oligodendrocyte myeilin glycoprotein (OMgp: reviewed in Yiu G. and He Z. Glial inhibition of CNS axon regeneration, *Nat. Rev. Neurosci.* 7: 617-627 (2006).). Thus severed axons attempting to regenerate across sites of injury, then through myelin rich white matter beyond injury sites and finally extending axonal "collateral" side branches from white matter into gray matter (in order to establish functional synaptic connections), must navigate through different domains of the injured CNS that contain multiple axon growth inhibitory molecules.

Small leucine rich proteoglycans (SLRP) of the extracellular matrix (EM) comprise an expanding family of proteoglycans and glycoproteins that now encompass five distinct groups (Hocking, A. M., et al. Leucine-rich repeat glycoproteins of the extracellular matrix. *Matrix Biol.* 17, 1-19 (1998); Lozzo R V. The biology of the small leucine-rich proteoglycans Functional network of interactive proteins. *J. Biol. Chem* 274, 18843-18846 (1999)). The SLRP family comprises about 17 genes that share structural homologies, such as cysteine residues, leucine rich repeats and at least one glycosaminoglycan side chain. Decorin and biglycan belong to class I, presenting similarities in their amino acid sequence, in the chondroitin or dermatan sulfate side chains and a typical cluster of cysteine residues at the N-terminus that form two disulfide bonds. Fibromodulin and lumican belong to class II, both presenting keratin sulfate and polyactosamines side chains, as well as clusters of tyrosine-sulfate residues at their N-terminal (Schaefer, L., et al. Biological functions of small leucine-rich proteoglycans: from genetics to signal transduction. *J. Biol. Chem* 283(31), 21305-21309, (2008)). Some SLRPs act as a growth factor reservoir in the extracellular matrix, modulating biological processes, such as cell proliferation and differentiations (Hocking, A. M., et al. Leucine-rich repeat glycoproteins of the extracellular matrix. *Matrix Biol.* 17, 1-19 (1998); Vogel, K. G., et al. Specific inhibition of type I and type II collagen fibrilogenesis by the small proteoglycan of tendon. *Biochem J.* 222, 587-597 (1984)). They are capable of inducing signaling cascades through tyrosine kinase, toll-like and TGF-β/BMP receptors (Schaefer, L., et al. Biological functions of small leucine-rich proteoglycans: from genetics to signal transduction. *J. Biol. Chem* 283(31), 21305-21309, (2008)).

Decorin is a naturally occurring SLRP that is found in the extracellular matrix (EM) of many tissue types in mammals, is a naturally occurring antagonist of scar formation (reviewed by Hocking, A. M., et al. Leucine-rich repeat glycoproteins of the extracellular matrix. *Matrix Biol.* 17, 1-19 (1998), and is known to inhibit the activity of at least three isoforms of TGF-β (Yamaguchi, Y., et al. Negative regulation of transforming growth factor-beta by the proteoglycan decorin. *Nature* 346, 281-284 (1990)). Decorin is also an antagonist of the epidermal growth factor (EGF) receptor tyrosine kinase (Santra, M., et al. Decorin binds to a narrow region of the epidermal growth factor (EGF) receptor, partially overlapping but distinct from the EGF-binding epitope. *J. Biol. Chem.* 277, 35671-35681 (2002)) and is known to have both anti-inflammatory and anti-fibrotic properties. After CNS injury, decorin is synthesized by astrocytes in the damaged CNS neuropil (Stichel, C. C., et al. Differential expression of the small chondroitin/dermatan sulfate proteoglycans decorin and biglycan after injury of the adult rat brain. *Brain Res* 704(2), 263-274 (1995)) and thus may represent an endogenous attempt to down-regulate cytokine activity and promote plasticity of neural circuits within the injured mammalian CNS.

In many cases where neurological function has been lost, such as in a spinal cord injury, there are currently no FDA (United States Food and Drug Administration) approved interventions to reverse the damage and to restore neurological function. Most treatments focus on preventing further injury. Accordingly, there remains a need in the art for novel therapies that promote robust levels of neurological functional recovery when administered to patients suffering from neurological conditions, including CNS injuries and/or diseases.

SUMMARY OF INVENTION

One embodiment of the invention relates to a method to treat a neurological condition in a patient by administering a small leucine-rich proteoglycan (SLRP) to the intrathecal cavity of the patient. In one aspect, the step of administering is conducted without direct administration of the SLRP to central nervous system tissues. In another aspect, the step of administering includes administering the SLRP to a portion of the intrathecal cavity selected from the cisterna cerebellomedullaris (cisterna magna), the intrathecal cavity at the cervical, thoracic, lumbar and sacral spinal cord levels, and infusion to the cerebral spinal fluid (CSF) surrounding the corda equina.

The SLRP can be selected from decorin, asporin, biglycan, fibromodulin, epiphycan, lumican, keratocan, osteroglycin, chondroadherin, proline arginine end leucine rich proteoglycan (PRELP), and combinations thereof. In one aspect, the SLRP is decorin, and the decorin can be chemically modified. In another aspect, the SLRP is a decorin-like peptide.

The neurological condition in the patient being treated can be a chronic neurological condition or a traumatic neurological condition. In various aspects, the neurological condition is a chronic neurological condition selected from amyotrophic lateral sclerosis (ALS), multiple sclerosis (MS), Alzheimer's disease, Parkinson's disease, transverse myelitis, cerebral palsy, chronic inflammatory demyelinating polyneuropathy, hydrocephalus, and motor neuron disease. In other aspects, the neurological condition is a traumatic neurological condition selected from traumatic brain injury, traumatic spinal cord injury, stroke, tethered spinal cord syndrome, and global hypoxic ischemia.

In yet other aspects, the step of administering the SLRP can be at various time points after the occurrence of a traumatic neurological condition. For example, the step of administering can be conducted shortly after the traumatic neurological condition, such as within about 24 hours. In addition, the step of administering the SLRP can be administered at longer times after traumatic neurological condition and still be effective. For example, the administration can be initiated after about 1 month after the occurrence of the traumatic neurological condition.

In still another aspect, the present method further includes an additional treatment for a traumatic neurological condition. The additional treatment for traumatic neurological condition can be administering anti-inflammatory agents, temperature reducing agents, immobilization, cell transplantation based therapies, cell infusion based therapies, implantation of biomaterials, intrathecal infusion of SLRP releasing nano-particles, exercise therapies, functional electrical stimulation based rehabilitative therapies, surgical interventions, clinically induced hypothermia based CNS therapies or gene therapy based interventions. In some aspects of the invention, the traumatic neurological condition in the patient is stabilized at the time of administration.

The step of administering a SLRP can include administering a bolus of the SLRP to the patient. Alternatively or in addition, the step of administering can include continuous delivery of the SLRP to the patient.

The methods of the present invention can result in recovery of neurological function in the patient. In one aspect, the method results in an indication, compared to a control, wherein the indication is an increase in axon extension and branching, an increase in neuronal dendrite extension, branching and spine formation, promotion of synaptogenesis within the injured or diseased central nervous system, upregulation of plasminogen protein levels, upregulation of plasmin protein levels, suppression of the axon growth inhibitory actions of glial scar, suppression of the synthesis of glial scar associated axon growth inhibitors, myelin and gray matter associated axon growth inhibitors, suppression of inflammation, suppression of astrogliosis, suppression of aberrant synthesis of multiple axon growth inhibitory chondroitin sulfate proteoglycans, suppression of fibrotic scar formation, suppression of glycosaminoglycan side chains (GAGs)/core protein levels of multiple axon growth inhibitor chondroitin sulfate proteoglycans (CSPGs) and de-sensitization of neurons to the influence of axon growth inhibitory molecules.

The patient in the invention can include any mammal, including human and non-human mammals.

Another embodiment of the invention relates to a kit for treating a neurological condition, that includes (a) a means for administering a SLRP to the intrathecal cavity of a patient; and (b) a SLRP. In one aspect, the means for administering can be an intrathecal pump, a catheter, tubing, cerebrospinal fluid-diverting shunt, a CSF reservoir-on/off valve-ventriculoperitoneal shunt (RO-VPS), nano-particles or combinations thereof. In one aspect of this embodiment, the SLRP can be decorin, small decorin-like peptides, asporin, biglycan, fibromodulin, epiphycan, lumican, keratocan, osteroglycin, chondroadherin, proline arginine end leucine rich proteoglycan (PRELP), or combinations thereof.

Yet another embodiment of the invention relates to composition that includes a first small leucine-rich proteoglycan (SLRP) and a second therapeutic compound for treating a neurological condition. In one aspect, the second therapeutic compound can be selected from a second SLRP that is different from the first SLRP, anti-inflammatory agents, temperature reducing agents, chondroitnases, lithium, hydrogels, neurotrophic growth factors designed to promote axon growth or remyelination of axons, anti-apoptotic agents to promote survival of CNS neurons and glia and combinations thereof. In one aspect, the first SLRP is decorin.

A further embodiment of the invention is a method for suppressing semaphorin 3A expression in injured central nervous system tissue, comprising administering to a patient a pharmaceutical composition to the intrathecal cavity of a patient, wherein the pharmaceutical composition comprises a SLRP and wherein semaphorin 3A expression is inhibited. In one aspect, the step of administering includes administering the SLRP to a portion of the intrathecal cavity selected from the cisterna cerebellomedullaris (cistern magna), the intrathecal cavity at the cervical, thoracic, lumbar and sacral spinal cord levels, and infusion to the cerebral spinal fluid (CSF) surrounding the corda equina. In one aspect, the step of administering is conducted with direct administration of the SLRP to central nervous system tissues. In one aspect of this embodiment, the SLRP is decorin.

DETAILED DESCRIPTION

Figure 1:
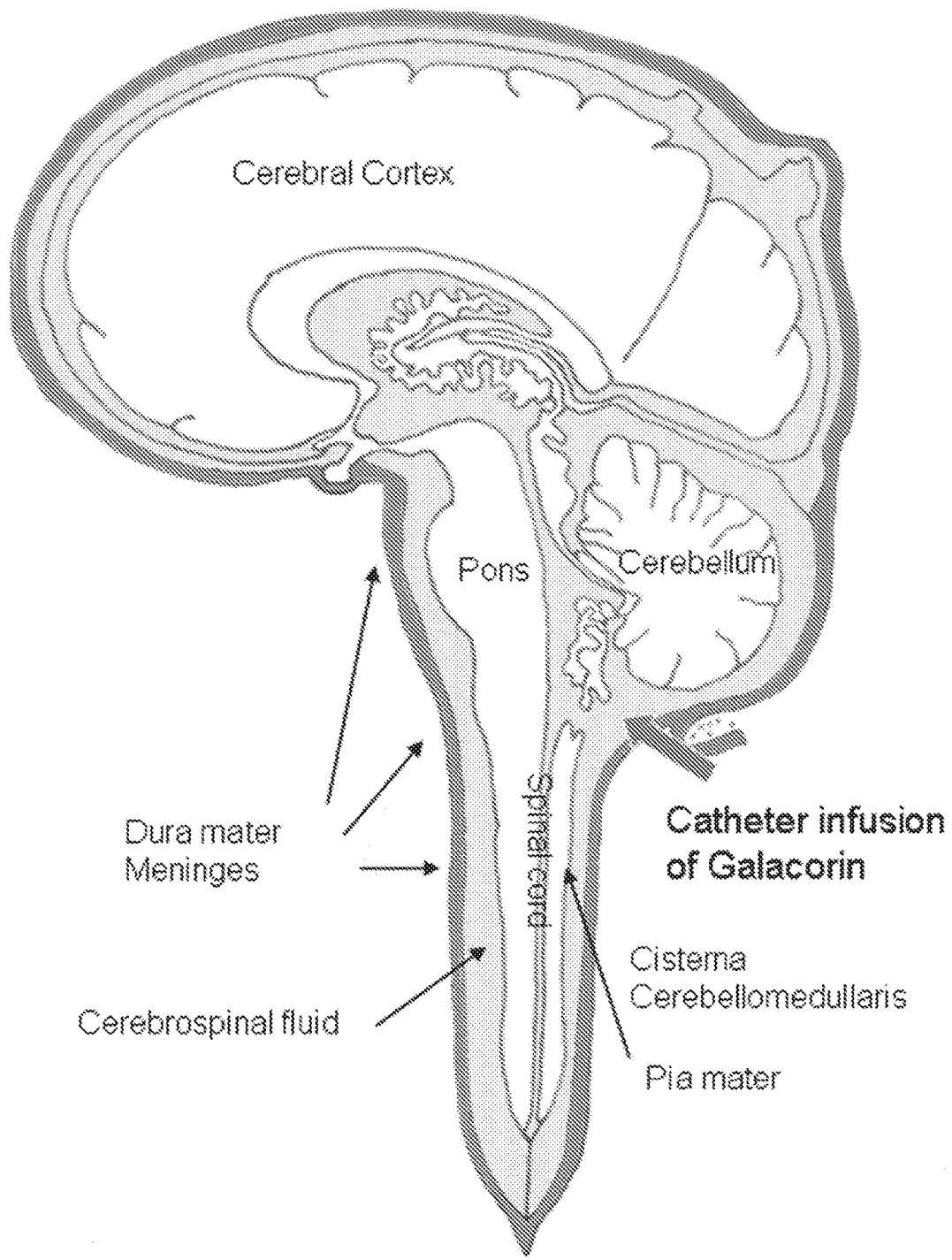
FIG. 1 GALACORIN™ infused via catheter to Cisterna Cerebellomedullaris (cisterna magna) CSF in humans to promote recovery of neurological function. (Schematic adapted from Grays Anatomy, Thirtieth American Edition). Dura mater Meninges (darkest shaded area); Cerebrospinal fluid (lighter shaded area).

The present invention is directed toward methods to treat neurological conditions in a patient. The invention includes administering a small leucine-rich proteoglycan (SLRP) to the intrathecal cavity (i.e. intrathecal space) of the patient.

A neurological condition generally refers to a disorder of the nervous system. Accordingly, these conditions include but are not limited to disorders involving muscles, structural disorders of the brain and spinal cord, structural disorders of the nerves in the face, trunk and limbs, as well as conditions which are not caused by structural disease such as many varieties of headaches and conditions such as epilepsy, fainting and dizziness. In one embodiment of the invention, the neurological condition is selected from acute neurological conditions, chronic neurological conditions and traumatic neurological conditions. In one embodiment, the neurological condition can include amyotrophic lateral sclerosis (ALS), multiple sclerosis (MS), Alzheimer's disease, Parkinson's disease, Transverse myelitis, cerebral palsy, chronic inflammatory demyelinating polyneuropathy, hydrocephalus and motor neuron disease. An acute neurological condition generally refers to a condition in which symptoms appear and change and/or worsen rapidly. These conditions are generally severe and sudden in onset. A chronic neurological condition generally develops and worsens over an extended period of time and is thus considered to be a long-developing condition. A traumatic neurological condition is a serious injury or shock to the body. In another embodiment of the invention the traumatic neurological condition includes but is not limited to traumatic brain injury, traumatic spinal cord injury, stroke, tethered spinal cord injury syndrome and global hypoxic ischemia.

In other embodiments of the present invention, practice of methods of the present invention will effectively treat neurological conditions. In the case of acute and chronic neurological conditions, effective treatment includes improving neurological function, stopping the decline in neurological function or slowing the decline in neurological function. In the case of traumatic neurological condition, methods of the present invention can stabilize a patient, alone or in combination with other treatments. In general, a traumatic neurological condition is stabilized when the condition no longer poses an immediate danger of death or harm to the patient and the patient's vital signs are stable (within normal limits).

Methods of the present invention may be used to treat a variety of different patients. In one embodiment of the invention, the patients can include all vertebrates. In a specific embodiment of the invention, the vertebrates are preferably mammals. In a preferred embodiment of the invention, patients include but are not limited to, mammals such as non-human mammals and humans. The non-human mammals include but are not limited to dogs and cats. The patients can have neurological conditions, such as acute neurological conditions, chronic neurological conditions or traumatic neurological conditions.

Methods of the present invention used to treat neurological conditions in a patient include a step of administering a SLRP to the patient, which can be accomplished in a variety of ways. In a preferred embodiment of the invention, the step of administering is conducted without direct administration of the SLRP to the central nervous system tissues of the patient. In general, nervous system tissue is the main component of the nervous system (brain, spinal cord and nerves which regulate and control body function). The central nervous system tissues can comprise the spinal cord, brain, cerebral cortex, cerebellar cortex, the meninges, glial cells, and choroid plexus.

In embodiments of the present invention, the step of administering can be administering the SLRP to a portion of the intrathecal cavity selected from the group consisting of cisterna cerebellomedullaris (cisterna magna), the intrathecal cavity at the cervical, thoracic, lumbar and sacral spinal cord levels, and infusion to the cerebral spinal fluid (CSF) surrounding the corda equina. In preferred embodiments, the SLRP is administered to the intrathecal cavity and to the cisterna cerebellomedullaris. The intrathecal cavity generally refers to the space under the arachnoid membrane which covers the brain and spinal cord of the patient. The arachonoid membrane is on the three meninges, the membranes that cover the brain and spinal cord. Cerebrospinal fluid flows under this membrane in the subarachnoid space.

In embodiments of the invention, the SLRP can be administered to the intrathecal cavity according to the present invention, by a variety of means. For example, a source of the SLRP can be contacted with the intrathecal cavity by means of a shunt or catheter to allow for delivery of the SLRP to the intrathecal cavity.

In embodiments of the invention, the step of administering is conducted after the occurrence of a traumatic neurological condition. In some embodiments, the step of administering is conducted as shortly after the incident causing the traumatic neurological condition as possible. For example, the step of administering can be conducted within about 1 hour, 2 hours, 3 hours, 4 hours, 5 hours, 6 hours, 9 hours, 12 hours, 18 hours or 24 hours after the incident. In other embodiments, the step of administering is conducted at longer times after the incident causing the traumatic neurological condition, and the method is still effective. For example, the administration can be initiated after about 1 day, 2 days, 3 days, 4 days, 5 days, 6 days, 7 days, 8 days, 9 days, 10 days, 20 days or 30 days and at more extended sub-acute (1 month) and long term chronic time points after the occurrence of the traumatic neurological condition. In still other embodiments, the administration is initiated at significantly longer times after the occurrence of a traumatic neurological condition. For example, the administration can be initiated after about 1 month, 3 months, 6 months, 1 year, 3 years, 5 years, 7 years, or 9 years after the occurrence of the traumatic neurological condition.

In still other embodiments, the step of administering may be conducted by administering a bolus of SLRP to the patient and/or continuous delivery of the SLRP to the patient over a period of time, such as over about 1 hour, about 2 hours, about 3 hours, about 4 hours, about 5 hours, about 6 hours, about 9 hours, about 12 hours, about 15 hours, about 18 hours, about 21 hours, about 24 hours or over a period of 8 days.

In considering the specific use of a SLRP, such as decorin for treatment of neurological conditions including CNS injuries or diseases, previous published studies in rat CNS injury models showed that decorin infusion was anti-inflammatory and lowered levels of scar-associated axon growth inhibitors (Davies, J. E., et al. Decorin Promotes Plasminogen/Plasmin Expression within Acute Spinal Cord Injuries and by Adult Microglia In Vitro. *J Neurotrauma* 23, 397-408 (2006); Davies, J. E., et al. Decorin suppresses neurocan, brevican, phosphacan and NG2 expression and promotes axon growth across adult rat spinal cord injuries. *Eur. J Neurosci.* 19, 1226-1242 (2004); Logan, A., et al. Decorin attenuates gliotic scar formation in the rat cerebral hemisphere. *Exp. Neurol.* 159, 504-510 (1999)). Notably however these previous studies of decorin administration to brain and spinal cord injuries relied on relatively traumatic direct injection of decorin into or through the parenchyma (tissues) of the acutely injured brain and spinal cord (Davies, J. E., et al. Decorin Promotes Plasminogen/Plasmin Expression within Acute Spinal Cord Injuries and by Adult Microglia In Vitro. *J Neurotrauma* 23, 397-408 (2006); Davies, J. E., et al. Decorin suppresses neurocan, brevican, phosphacan and NG2 expression and promotes axon growth across adult rat spinal cord injuries. *Eur. J Neurosci.* 19, 1226-1242 (2004); Logan, A., et al. Decorin attenuates gliotic scar formation in the rat cerebral hemisphere. *Exp. Neurol.* 159, 504-510 (1999)). Importantly, these methods of administering decorin were not shown to result in recovery of neurological function (Davies, J. E., et al. Decorin Promotes Plasminogen/Plasmin Expression within Acute Spinal Cord Injuries and by Adult Microglia In Vitro. *J Neurotrauma* 23, 397-408 (2006); Davies, J. E., et al. Decorin suppresses neurocan, brevican, phosphacan and NG2 expression and promotes axon growth across adult rat spinal cord injuries. *Eur. J Neurosci.* 19, 1226-1242 (2004); Logan, A., et al. Decorin attenuates gliotic scar formation in the rat cerebral hemisphere. *Exp. Neurol.* 159, 504-510 (1999)).

Accordingly, methods of the present invention comprise administering SLRPs to the intrathecal cavity of the patient, preferably to the cisterna cerebellomedullaris which provides a means of simultaneously distributing a SLRP to the CSF of both the brain and spinal cord. SLRPs are a proteoglycan family made up of several members which guide matrix assembly and organization through protein:protein and/or protein:carbohydrate interactions. The family is categorized by the presence of several conserved regions found within their core proteins. These conserved regions include a central leucine rich repeat domain, four cysteine residues within the amino-terminus and 2 cysteine residues within the carboxy-terminus. (Johnson, J. M., et al. Small leucine rich repeat proteoglycans (SLRPs) in the human sclera: Identification of abundant level of PRELP *Mol. Vis.* 12, 1057-1066 (2006)) SLRPs are tissue organizers by orienting and ordering various collagenous matrices during ontogeny, wound repair, and cancer and interact with a number of surface receptors and growth factors, thereby regulating cell behavior (Lozzo R V. The biology of the small leucine-rich proteoglycans Functional network of interactive proteins. *J. Biol. Chem* 274, 18843-18846 (1999)). In one embodiment of the present invention, the SLRP is selected from the group consisting of decorin, asporin, biglycan, fibromodulin, epiphycan, lumican, keratocan, osteroglycin, chondroadherin, proline arginine end leucin rich proteoglycan (PRELP), and combinations thereof. In a preferred embodiment, the SLRP is decorin. A preferred form of decorin is GALACORIN™ (Catalent Pharma Solutions, Somerset, N.J.) which is a form of decorin core-protein that lacks a chondroitin or dermatan sulfate glycosaminoglycan (GAG) side chain.

Reference herein to SLRPs includes SLRP-like peptides as well as the native proteins. For example, reference to decorin includes small decorin-like peptides. These small decorin-like peptides can be derived from the amino acid sequence for decorin core protein in regulating angiogenesis and interacting with TGF betas and extracellular matrix fibronectin (Schonherr E. et al. Decorin core protein fragment Leu155-Val260 interacts with TGF-beta but does not compete for decorin binding to type I collagen, *Arch. Biochem. Biophys.* 355: 241-248 (1998); Fan H. K. et al, Decorin derived antiangiogenic peptide LRR5 inhibits endothelial cell migration by interfering with VEGF-stimulated NO release, *Int. J Biochem. Cell Biol.* 40; 2120-2128 (2008); Sulochana K. N et al. Peptides derived from human decorin leucine-rich repeat 5 inhibit angiogenesis, *J Biol. Chem.* 280; 27935-27948(2005); Schmidt G. et al. Interaction of the small proteoglycan decorin with fibronectin. Involvement of the sequence NKISK of the core protein. *Biochem. J* 280 (Pt 2); 411-414(1991)). The ability of these small decorin-like peptides to promote repair of injured and diseased mammalian central nervous system has not been reported. Likewise, reference to asporin includes the native asporin protein and asporin-like peptides.

In other embodiments, SLRPs used in the present invention can be chemically modified to alter the chemical nature of the SLRP. For example a small peptide derived from the core protein of a SLRP that retains a specific beneficial bioactivity specific to the SLRP from which is was derived. For example, a SLRP can be PEGylated (covalent attachment of polyethylene glycol polymer chains to prolong its circulatory time and aid uptake into tissues). SLRPs can be PEGylated by methods known to those of skill in the art. Examples include but are not limited to the selective PEGylation at a unique glycosylation site of the target protein as well as the selective PEGylation of a non-natural amino acid that has been engineered into the target proteins. In some cases it has been possible to selectively PEGylate the N-terminus of a protein while avoiding PEGylation of lysine side chains in the target protein by carefully controlling the reaction conditions. In yet another approach for the site-specific PEGylation of target proteins is the introduction of cysteine residues that allow selective conjugation.

Decorin is expressed in many tissue types and has been shown to suppress fibrotic scarring in several tissue disorders including brain and spinal cord injuries. Decorin is capable of inhibiting transforming growth factor-beta activity and modulating the activity of downstream signaling pathways linked to several erythroblastic leukaemia viral oncogene homologue (ErbB) receptor family members. Infusion of human recombinant decorin core protein into acute spinal cord injury in adult rats can suppress the levels of multiple axon growth inhibitory chondroitin sulfate proteoglycans (CSPGs) and render injury sites permissive for axon growth.

In other embodiments of the present invention, the method comprises use of a fusion protein comprising a SLRP and another functional protein. For example, a SLRP can be fused with a Coxsackie virus and adenovirus receptor (CAR) (Jarvinen T. A. and Ruoslahti E. Target-seeking antifibrotic compound enhances wound healing and suppresses scar formation in mice, *Proc. Natl. Acad. Sci. U. S. A* 107: 21671-21676 (2010)) a vascular targeting peptide designed to promote the uptake of SLRPs such as decorin or small bioactive peptides derived from SLRP core proteins into the injured CNS parenchyma, meninges or dorsal and ventral peripheral nervous system roots.

Some aspects of the method to treat neurological conditions in a patient by administering a SLRP to the intrathecal cavity of the patient include increasing the density of cortical spinal tract (CST) axons in the patient. In the case of traumatic injuries, the effect of increasing the density of supraspinal projecting axons (from brain to spinal cord) such as CST axons can occur within the brain and spinal cord above, adjacent to and below the injury site. Other aspects of the method to treat neurological conditions in a patient by administering a SLRP to the intrathecal cavity of the patient include increasing the density of synapsin-1 in the patient. In the case of traumatic injuries, the effect of increasing the density of synapsin-1, indicating an increase in numbers of active synapses, can occur in all laminae of spinal cord gray matter as well as in and around the motor neuron pools within ventral horn gray matter at spinal levels above and below sites of injury.

Other methods of the present invention are directed toward a method for suppressing semaphorin 3A (Sema3A) expression in injured central nervous system tissue comprising administering a pharmaceutical composition comprising a SLRP to the intrathecal cavity of a patient. In one aspect of the method, the Sema3A expression is inhibited. Sema3A is the member of the secreted class 3 semaphorins which are known to comprise a large family of secreted and membrane bound glycoproteins that function in axon guidance, fasciculation and synapse formation. Sema3A is expressed during develop and in adulthood and can function as a potent chemorepellent for select neuronal populations in the central and peripheral nervous system. Sema3A has been shown to be unregulated at sites of traumatic central nervous system injury where it is thought to act as an inhibitor of axonal regeneration by promoting growth cone collapse ((Pasterkamp R. J. et al. Expression of the gene encoding the chemorepellent semaphorin III is induced in the fibroblast component of neural scar tissue formed following injuries of adult but not neonatal CNS, *Mol. Cell Neurosci* 13: 143-166(1999); Pasterkamp R. J. and. Kolodkin A. L, Semaphorin junction: making tracks toward neural connectivity, *Curr. Opin. Neurobiol.* 13:79-89 (2003); Andrews E. M. et al. Alterations in chondroitin sulfate proteoglycan expression occur both at and far from the site of spinal contusion injury, *Exp. Neurol.* ePub ahead of print (2011); Tang X., et al. Changes in distribution, cell associations, and protein expression levels of NG2, neurocan, phosphacan, brevican, versican V2, and tenascin-C during acute to chronic maturation of spinal cord scar tissue. *J. Neurosci. Res.* 71: 427-444(2003)).

Other embodiments of the present invention comprise treating a neurological condition by administering a SLRP to the intrathecal cavity of the patient in combination with an additional treatment for a traumatic neurological condition. In a preferred embodiment, the additional treatment for treating a traumatic neurological condition comprises administering anti-inflammatory agents, temperature reducing agents, immobilization, cell transplantation based therapies, cell infusion based therapies, implantation of biomaterials, intrathecal infusion of SLRP releasing nanoparticles, exercise and functional electrical stimulation based rehabilitative therapies, surgical interventions, clinically induced hypothermia based CNS therapies and gene therapy based interventions. Anti-inflammatory agents are well known in the art and include but are not limited to non-steroidal anti-inflammatory drugs (NSAIDS) such as aspirin, ibuprofen and naproxen, and analgesics such as acetaminophen. Temperature reducing agents are also well known in the art and may include ibuprofen and acetaminophen.

In some embodiments of the present invention, treating a neurological condition can include, in addition to the administration of a SLRP, administration of a second therapeutic compound for treating a neurological condition. Such second therapeutic compounds can be a second SLRP that is different from the first SLRP, anti-inflammatory agents, temperature reducing agents, chondroitinase enzymes, neurotrophic growth factors designed to promote axon growth or remyelination of axons, and anti-apoptotic agents to promote survival of CNS neurons and glia and combinations thereof.

A further embodiment of the present invention, is administration of a SLRP to the intrathecal cavity wherein the SLRP is attached to a self assembling peptide scaffold or matrix (SAP) (Cigognini D., et al. Evaluation of early and late effects into the acute spinal cord injury of an injectable functionalized self-assembling scaffold *PLoS ONE* 6:e19782 (2011)). SAPs are a category of peptides which undergo spontaneous assemble into ordered nanostructures. The SAPs provide a scaffold for the SLPRs and presents an active molecule with improved biological activity. In other embodiments, the SLRP-SAP complex is infused into the intrathecal cavity. In still other embodiments, the SLRP-SAP is a decorin-SAP complex.

In embodiments of the present invention, the present methods can result in recovery of neurological function in the patient. In yet other embodiments, the methods can result in one or more of the following indications, compared to a control, an increase in axon extension and branching, upregulation of plasminogen protein levels, upregulation of plasmin protein levels, suppression of the synthesis of glial scar associated axon growth inhibitors, suppression of the axon growth inhibitory actions of glial scar, myelin and gray matter associated axon growth inhibitory molecules, suppression of inflammation, suppression of astrogliosis, suppression of aberrant expression of multiple axon growth inhibitory chondroitin sulfate proteoglycans, suppression of fibrotic scar formation and suppression of glycosaminoglycan side chains (GAGs)/core protein levels of multiple axon growth inhibitor chondroitin sulfate proteoglycans (CSPGs), and de-sensitization of neurons to the influence of axon growth inhibitory molecules within the injured or diseased adult mammalian central nervous system in order to promote plasticity and function of neural circuits.

The present invention is also directed toward a kit for treating a neurological condition. In one embodiment, the kit comprises a means for administering a SLRP to the intrathecal cavity of a patient. In one embodiment, the means for administering comprises an intrathecal pump. In yet other embodiment, the means for administering comprises a catheter. In yet another embodiment, the means for administering a SLRP comprises a cerebrospinal fluid-diverting shunt. In yet another embodiment, the means for administering a SLRP comprises a CSF reservoir-on/off valve-ventriculoperitoneal shunt (RO-VPS). In yet another embodiment, the means for administering comprises tubing. In yet another embodiment, the means of administering the SLRP comprises release by nano-particles injected or infused into the intrathecal cavity of the CNS. In yet another embodiment, the SLRP administered by the kit is selected from the group consisting of decorin, small decorin-like peptides, asporin, biglycan, fibromodulin, epiphycan, lumican, keratocan, osteroglycin, chondroadherin, proline arginine end leucin rich proteoglycan (PRELP), and peptides with SLRP bioactivity and combinations thereof.

The present invention is also directed toward a novel composition comprising decorin and an additional or second therapeutic compound for treating neurological conditions. Such additional compounds can include, but are not limited to a second SLRP that is different from the first SLRP, anti-inflammatory agents, temperature reducing agents, neurotrophic growth factors designed to promoted axon growth and remyelination of axons, anti-apoptotic agents to promote survival of CNS gila, artificial cerebrospinal fluid, chondroitinases, lithium hydrogels and combinations thereof. Chondroitinases are enzymes that catalyze the elimination of glucuronate residues from chondroitin A, B, and C and is a treatment of chondroitin sulfate proteoglycans (proteins in the extracellular matrix among cells where they affect neural activity) that have been used for treatment of pre-clinical experimental spinal injuries in animals. Lithium can enhance neuronal regeneration and differentiation (Wong et al., Spinal Cord; 49 2011). Hydrogels can improve healing when injected into a spinal cord injury site (Chen, B. K. et al. Comparison of polymer scaffolds in rat spinal cord: a step toward quantitative assessment of combinatorial approaches to spinal cord repair, *Biomaterials* 32:8077-8086 (2011)).

In another embodiment of the present invention, the SLRP is selected from the group consisting of decorin, a modified form of decorin, a chemically modified form of decorin, a decorin derived peptide and a peptide with SLRP bioactivity.

In addition to regenerating severed axons, strategies that can also promote "neural plasticity" i.e. the ability of surviving axons within neural circuits to sprout and form new synapses are likely to also promote recovery of neurological function. Thus therapeutic strategies that can suppress the formation of axon growth inhibitory scar formation at acute time points after injury and also promote the plasticity of regenerating and surviving neural circuits in the acute and chronically injured or diseased CNS after scar tissue has already formed can provide significant recovery of neurological functions.

Active molecules of the present invention (SLRPs), specifically including decorin, a naturally occurring antagonist of scar formation, are highly effective at suppressing inflammation, astrogliosis within injury margins, synthesis of multiple inhibitory CSPGs and fibrous scar formation when infused into acute spinal cord injuries in rats (Davies, J. E., et al. Decorin suppresses neurocan, brevican, phosphacan and NG2 expression and promotes axon growth across adult rat spinal cord injuries. Eur. J. Neurosci. 19, 1226-1242 (2204)). More importantly direct infusion of decorin to the spinal cord permitted the rapid growth of axons across sites of injury in just 4 days (Davies, J. E., et al. Decorin suppresses neurocan, brevican, phosphacan and NG2 expression and promotes axon growth across adult rat spinal cord injuries. Eur. J. Neurosci. 19, 1226-1242 (2004)). The ability of decorin to inhibit both transforming growth factor betas (Yamaguchi, Y., et al. Negative regulation of transforming growth factor-beta by the proteoglycan decorin. Nature 346, 281-284 (1990)) and epidermal growth factor receptor signaling (Csordas, G., et al. Sustained down-regulation of the epidermal growth factor receptor by decorin. A mechanism for controlling tumor growth in vivo. J. Biol. Chem. 275, 32879-32887 (2000)) are likely molecular mechanisms through which decorin can suppress CNS scar formation as TGFβs and the EGFR ligands, EGF and TGFα, have all been shown to upregulate CSPG synthesis by astrocytes in vitro (Asher, R. A., et al. Neurocan is upregulated in injured brain and in cytokine-treated astrocytes, J. Neurosci. 20, 2427-2438 (2000); Properzi, F., et al. Chondroitin 6-sulphate synthesis is up-regulated in injured CNS, induced by injury-related cytokines and enhanced in axon-growth inhibitory glia, Eur. J. Neurosci. 21, 378-390 (2005); Schnadelbach, O., et al. Expression of DSD-1-PG in primary neural and glial-derived cell line cultures, upregulation by TGF-beta, and implications for cell-substrate interactions of the glial cell line Oli-neu. Gila 23, 99-119 (1998)) and promote astrogliosis (physical mis-alignment of astrocyte processes) in vivo (Rabchevsky, A. G., et al. A role for transforming growth factor alpha as an inducer of astrogliosis. J. Neurosci. 18, 10541-10552 (1998)). Through specific interactions with the Erb B4 receptor, decorin can suppress the expression of semaphorin 3A (Minor, K. H., et al. Decorin, erythroblastic leukaemia viral oncogene homologue B4 and signal transducer and activator of transcription 3 regulation of semaphorin 3A in central nervous system scar tissue, Brain (2010), another important scar associated inhibitory molecule expressed by invading fibroblasts within the center of brain and spinal scar tissue (R. J. Pasterkamp, A. L. Kolodkin, Semaphorin junction: making tracks toward neural connectivity. Curr. Opin. Neurobiol. 13 (2003) 79-89; F. De Winter, F. De., et al. Injury-induced class 3 semaphorin expression in the rat spinal cord, Exp. Neurol. 175 (2002) 61-75; Pasterkamp, R. J., et al. Role for semaphorin III and its receptor neuropilin-1 in neuronal regeneration and scar formation?, Prog. Brain Res. 117 (1998) 151-170).

In addition to lowering the levels of multiple inhibitory molecules at sites of CNS injury, other potential means of promoting the regeneration of severed axons and plasticity of surviving neural circuits are to remove the inhibitors, activate growth factors to overcome the inhibitors or directly change the sensitivity of axons to the inhibitors.

Infusion of human decorin directly into spinal cord injuries of adult rats can significantly increase spinal levels of the serine protease Plasmin (Davies J. E., et al. Decorin promotes plasminogen/plasmin expression within acute spinal cord injuries and by adult microglia in vitro. J Neurotrauma. 23 (2006) 397-408). Plasmin is an enzyme that is known to have the ability to breakdown inhibitory CSPGs (Wu, Y. P., et al. The tissue plasminogen activator (tPA)/plasmin extracellular proteolytic system regulates seizure-induced hippocampal mossy fiber outgrowth through a proteoglycan substrate, J. Cell Biol. 148 (2000) 1295-1304) and collagen IV {Mackay, 1990 6466/id}, a major component of glial scar basal lamina (Stichel, C. C., et al. Basal membrane-depleted scar in lesioned CNS: characteristics and relationships with regenerating axons, Neuroscience 93 (1999) 321-333). Plasmin can also activate several matrix metalloproteinases (MMPs) (Murphy, G., et al. The role of plasminogen activators in the regulation of connective tissue metalloproteinases. Ann. N. Y. Acad. Sci. 667 (1992) 1-12) that can degrade basal lamina and promote axon growth in the presence of inhibitory CSPGs (Ferguson, T. A., and Muir, D. MMP-2 and MMP-9 increase the neurite-promoting potential of schwann cell basal laminae and are upregulated in degenerated nerve, Mol. Cell Neurosci. 16 (2000) 157-167).

The balance between axon growth promoting and inhibitory cues has long been thought to play an important role in regulating the ability of regenerating axons to traverse CNS injuries (Ramon y Cajal, S. Degeneration and regeneration of the nervous system, Oxford University Press, London, U K, 1928). It is likely that neurotrophin growth factors, transiently expressed within CNS injuries (Nakamura, M. and Bregman, B. S. Differences in neurotrophic factor gene expression profiles between neonate and adult rat spinal cord after injury, Exp. Neurol. 169 (2001) 407-415), promote the sprouting of cut axons as first described by Ramon y Cajal and that the rapid upregulation of scar associated axon growth inhibitors such as the CSPGs results in the ultimately abortive nature of the sprouting (Davies, S. J., et al. Robust regeneration of adult sensory axons in degenerating white matter of the adult rat spinal cord, J. Neurosci. 19 (1999) 5810-5822; Davies, S. J. and Silver, J. Adult axon regeneration in adult CNS white matter [letter; comment], Trends Neurosci. 21 (1998) 515; S. J. Davies, S. J., et al. Regeneration of adult axons in white matter tracts of the central nervous system, Nature 390 (1997) 680-683). Increasing growth promoting cues by delivery of exogenous neurotrophins to either cell bodies of axotomized neurons (Hiebert. G. W., et al. Brain-derived neurotrophic factor applied to the motor cortex promotes sprouting of corticospinal fibers but not regeneration into a peripheral nerve transplant. J. Neurosci. Res. 69 (2002) 160-168; Plunet, W., et al. Promoting axonal regeneration in the central nervous system by enhancing the cell body response to axotomy, J. Neurosci. Res. 68 (2002) 1-6) or in the vicinity of injury sites in combination with cellular bridges (Oudega, M. and Hagg, T. Nerve growth factor promotes regeneration of sensory axons into adult rat spinal cord, Exp. Neurol. 140 (1996) 218-229); reviewed in (Bregman, B. S., et al. Transplants and neurotrophic factors prevent atrophy of mature CNS neurons after spinal cord injury, Exp. Neurol. 149 (1998) 13-27; Murray, M., et al. Transplantation of genetically modified cells contributes to repair and recovery from spinal injury, Brain Res. Brain Res. Rev. 40 (2002) 292-300) have been shown to promote axon growth across CNS scar tissue. Neurotrophins also promote axon growth in vitro in the presence of myelin and myelin associated glycoprotein (MAG) (Cai, D., et al. Prior exposure to neurotrophins blocks inhibition of axonal regeneration by MAG and myelin via a cAMP-dependent mechanism, Neuron 22 (1999) 89-101). Mature, axon growth promoting neurotrophins are derived from pro-neurotrophins by post-translational enzymatic cleavage (Edwards, R. H., et al. Processing of the native nerve growth factor precursor to form biologically active nerve growth factor, J Biol. Chem. 263 (1988) 6810-6815). Notably, proNGF (pro-peptide of human Nerve Growth Factor) and proBDNF (precursor to Brain-Derived Neurotrophic factor) are cleaved by plasmin and selective matrix metalloproteinases (MMPs) (Dougherty, K. D., et al. Brain-derived neurotrophic factor in astrocytes, oligodendrocytes, and microglia/macrophages after spinal cord injury, *Neurobiol. Dis.* 7 (2000) 574-585; Lee, R., et al. Regulation of cell survival by secreted proneurotrophins, *Science* 294 (2001) 1945-1948; Pang, P. T., et al. Cleavage of proBDNF by tPA/plasmin is essential for long-term hippocampal plasticity, *Science* 306 (2004) 487-491). Decorin-induced increases in plasmin within the injured or diseased CNS may therefore increase the levels of mature neurotrophins available to promote axon regeneration and plasticity in the acute and chronically injured or diseased spinal cord and brain.

Decorin can have a direct effect on neurons and effectively de-sensitize them to the axon growth inhibitory effects of multiple CSPGs and myelin associated inhibitors (Minor, K., et al. Decorin promotes robust axon growth on inhibitory CSPGs and myelin via a direct effect on neurons, *Neurobiol. Dis.* 32 (2008) 88-95). Robust increases in axon growth of 14.5 fold and 4.8 fold were observed for decorin treated adult sensory neurons grown on axon growth inhibitory scar CSPGs and myelin respectively (Minor, K., et al. Decorin promotes robust axon growth on inhibitory CSPGs and myelin via a direct effect on neurons, *Neurobiol. Dis.* 32 (2008) 88-95). The potential to promote axon growth despite the presence of CSPGs and myelin associated inhibitors makes decorin infusion to injured CNS tissues an important attribute for use as potential therapy for promoting axon regeneration and plasticity of connection in the sub-acute and chronically injured CNS where levels of these inhibitory molecules are known to be high in white and gray matter (Tang, X., et al. Changes in distribution, cell associations, and protein expression levels of NG2, neurocan, phosphacan, brevican, versican V2, and tenascin-C during acute to chronic maturation of spinal cord scar tissue, *J. Neurosci. Res.* 71 (2003) 427-444; Schwab, M. E. Nogo and axon regeneration. *Curr. Opin. Neurobiol.* 14 (2004) 118-124). Data presented in the examples herein show that treatment of adult rats with contusion spinal cord injuries via intrathecal infusion of decorin using the novel treatment paradigm of the present invention can promote robust sprouting of axons within the spinal cord, synaptic plasticity on spinal motor neurons and robust recovery of a variety of locomotor functions.

As demonstrated in the Examples below, the ability of intrathecal infusion of human decorin to promote functional recovery in a clinically-relevant rodent cervical spinal cord contusion injury model was tested. In seeking to establish a clinically relevant means of administering decorin to the injured central nervous system, the human recombinant decorin core protein was intrathecally administered to separate sets of spinal cord injured rats commencing immediately after injury, 12 days post spinal cord injury and 1 month after injury. Notably at the 12 day and 1 month post injury time points, axon growth inhibitory central nervous system scar tissue is already well-established and the opportunity to promoting significant neuroprotection of injured neurons is greatly reduced. As such, the ability of decorin to promote recovery via mechanisms that involve promotion of plasticity of connection of surviving neural circuits was evaluated. Decorin treatment of adult spinal cord injured rats resulted in robust functional recovery of locomotor functions as measured by Grid Walk/horizontal ladder and CatWalk analyses. CatWalk analysis of rats treated at 12 days after injury demonstrated recovery in both the fore- and hindlimbs on the injured side following decorin treatment that correlated with a ~85% recovery of Grid Walk/horizontal ladder performance scores. In particular the remarkable recovery of both fore and hind limb digit use in decorin treated spinal cord injured rats has important implications for the potential ability of intrathecal decorin treatment to promote recovery of hand and foot digit function in humans with spinal cord injuries. As provided in the data in the Example section the functional recovery observed in spinal cord injured rats treated a full 12 days after injury correlated with increased density of sensori-motor cortical spinal tract (CST) axons adjacent to and below the injury site and also increased density of synapsin-1 (a protein expressed within active synapses) in the ventral horn gray matter below sites. These findings further support intrathecal infusion of decorin as a treatment of the traumatically injured or diseased adult human central nervous system (brain and spinal cord). Importantly the ability of decorin to promote plasticity of important motor control circuits, such as the corticospinal tract and the density of active synapses on spinal motor neurons, extends the therapeutic window for decorin intrathecal infusion in promoting functional recovery to sub-acute and chronic central nervous system injuries.

The following examples are provided for the purposes of illustration and are not intended to limit the scope of the present invention.

EXAMPLES

Example 1

This example demonstrates the effect of treatment with decorin in accordance with the present invention on the ability of rats with cervical spine injuries to cross a Gridwalk/Horizontal Ladder compared to untreated rats.

Figure 2:
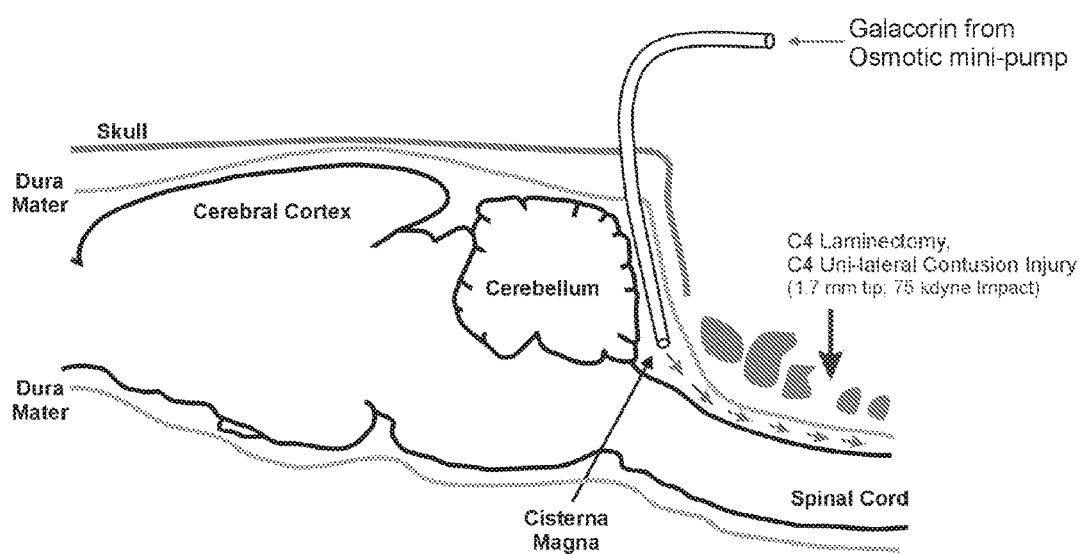
FIG. 2 Schematic showing experimental method of infusion of GALACORIN™ to the cisterna magna cerebrospinal fluid in adult spinal cord injured rats. Note that infusion to the cisterna magna avoids damage associated with contact of the catheter with the pial surface of the spinal cord.

Human decorin core protein, GALACORIN™ was tested in a delayed (sub-acute) treatment protocol for adult rats with cervical spinal cord injuries. Experimental spinal cord injuries were conducted using a computer controlled Infinite Horizon (IH) Impactor device (Precision Systems and Instrumentation, LLC) to generate a moderately severe unilateral contusion injury at the cervical (vertebral levels C4-C5; right sided unilateral contusion; tip diameter of 1.7 mm; 75 kdyne force; Displacement 1.1 mm) level of the spinal cord in adult Sprague Dawley rats (three-month old females). Beginning at a time point of twelve days after spinal cord injury, spinal cord injured rats (n=9) were treated with GALACORIN™ using the novel treatment paradigm where GALACORIN™ was infused into the cerebral spinal fluid (CSF) and not directly into central nervous system tissues of the spinal cord or brain (FIG. 2). To achieve CSF delivery of GALACORIN™, a small diameter cannula was surgically implanted into the cisterna magna of rats via a small burr hole drilled into the occipital bone of the skull (FIGS. 1 and 2). Approximately 20% (0.1 ml) of the total volume of CSF was removed and replaced with phosphate buffered saline (PBS) vehicle containing GALACORIN™ at concentration of 5 mg/ml (i.e. 1 mg of GALACORIN™). Cannulae were then anchored to the skull using dental cement and attached to Alzet osmotic pumps pre-loaded with saline containing GALACORIN™ at a concentration of 5 mg/ml for continuous intrathecal delivery at a rate of 0.1 mg GALACORIN™ per day for 8 days. A total of 1.43 mg of GALACORIN™ was therefore administered over the 8 day period of infusion. Control groups of untreated spinal cord injured rats consisted of those that received a cannula alone to the cisterna magna (control group 1: n=9 rats) or cannula to cisterna magna plus PBS infusion (control group 2: n=7 rats).

Figure 3:
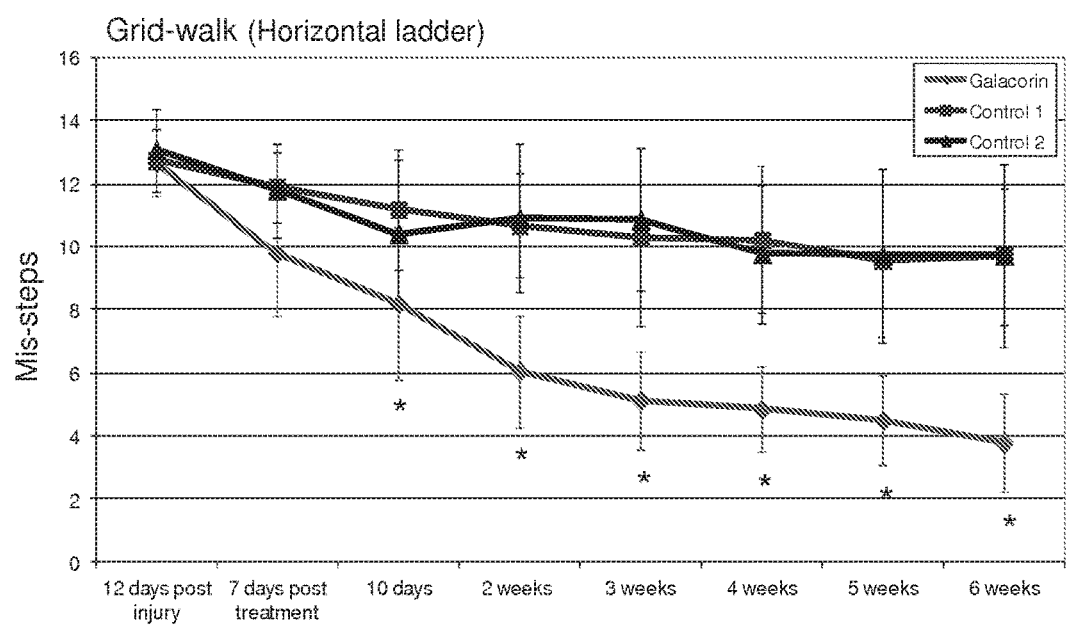
FIG. 3 Delayed GALACORIN™ infusion to cisterna magna starting at 12 days post-injury promotes robust recovery of locomotor neurological function in spinal cord injured adult rats. Note that the numbers of mis-steps made by GALACORIN™ treated rats continues to improve for several weeks after the 8 day period of GALACORIN™ infusion (data not shown). (*) denotes statistically significant difference in average scores between GALACORIN™ treated spinal cord injury (SCI) rats and Control 1 group untreated SCI rats. Statistical analysis: 2 way repeated measures ANOVA followed by multiple comparisons Holm-Sidak post test (p<0.05).

Following surgery, both GALACORIN™-treated and untreated rats underwent neurological behavioral testing over a period of 6 weeks. The Grid-walk or horizontal ladder test is a widely recognized stringent test of volitional paw placement locomotor recovery in spinal cord injured rodents where the average numbers of mistakes (falls) made by the rats making three passes of a meter long ladder is recorded. Grid walk neurological functional recovery outcomes (FIG. 3 and Table 1) clearly demonstrate a robust reduction in the numbers of missteps (mistakes) over time made by GALACORIN™-treated animals compared to either groups of control untreated spinal cord injured animals. At the 6 week endpoint after commencing GALACORIN™ treatment at 12 days after injury, GALACORIN™-treated rats showed a robust 61% reduction in numbers of mistakes compared to scores achieved by untreated control spinal cord injured rats that received a cannula alone to the cisterna magna (control group 1) or those infused in an identical manner with PBS vehicle alone (control group 2).

TABLE 1

| Experimental Group | Pre-Treatment Grid-walk mis-steps | 6 weeks post-treatment Grid-walk mis-steps |
|---|---|---|
| SCI + Galacorin (n = 9 rats) | 12.67 (SD +/− 1.04) | 3.78 (SD +/− 1.56) |
| Control 1 SCI + cannula (n = 9 rats) | 12.74 (SD +/− 0.10) | 9.70 (SD +/− 2.16) |
| Control 2 SCI + PBS (n = 7 rats) | 13.07 (SD +/− 1.29) | 9.71 (SD +/− 2.89) |

SD = Standard Deviation

Histological analysis of a pilot set of 4 rats that received an identical contusion spinal cord injury followed by immediate infusion of GALACORIN™ labeled with Alexa-488 to the cisterna magna, showed that GALACORIN™ administered in this way becomes localized to both injured spinal tissues as well as the surrounding meninges (Dura mater and arachnoid) and peripheral nervous system roots (dorsal and ventral roots). In this analysis a right side uni-lateral C4 contusion injury was made with an Infinite Horizon Impactor of adult three-month female rats (n=4) with acute infusion of Alexa-488 labeled GALACORIN™ to cisterna magna. The histological analysis was conducted at 18 hours post infusion. The analyzed histological image was a cross-section at the C5 spinal level (just caudal to the site of injury).

Example 2

This example is a CatWalk analysis of locomotor recovery of decorin treated spinal cord injured rats compared to non decorin treated (control) spinal cord injured rats. Comparison of treated and untreated animals with biotinylated dextran amine (BDA) labeling of spinal cord tissues was also conducted. Automated quantitative gait analysis was performed for all experimental groups using the CatWalk XT system (Version 8.1, Noldus Information Technology, Leesburg, Va. USA). The CatWalk system has been previously described in extensive detail (F. P. Hamers, et al. CatWalk-assisted gait analysis in the assessment of spinal cord injury. *J. Neurotrauma* 23, 537-548 (2006)). The system hardware consists of a translucent illuminated glass walkway under which a video camera (Fujinon Corporation, Japan) records the rats' paw prints as they cross the walkway. CatWalk data acquisition and analyses were carried out by individuals that were blinded with respect to treatment groups. Three runs that were deemed compliant were collected for each animal at each time point and the average for each parameter determined. Compliancy was determined based on total time used to cross the walkway and variance in speed of walking. The minimum run length was 2 seconds; the maximum length was 12 seconds, and the maximum variance in speed of walking 60%. The camera was positioned such that the length of the walkway measured 70 cm. Animals from all groups were tested immediately prior to injury, immediately prior to treatment at 12 days post-injury, and at 5 weeks post-injury. The following parameters were analyzed: print area, print area at maximum contact, print intensity, maximum contact relative to stance, and maximum intensity at maximum contact. Video files of compliant runs from all groups were processed using Cat-Walk XT 8.1 software to identify individual pawprint and gait patterns. All parameters except digit use were determined by the Catwalk software. Digit use was determined by acquiring images of prints at the point of Maximum Contact as defined by the software. Images of pawprints at maximum contact for each limb were selected randomly in a serial fashion, where 2 pawprints were selected per compliant run for a total of 6 randomly selected pawprints for all four limbs. This randomized selection was carried out on pawprint images collected from all animals at the 3 assessment time-points. Pawprint images at maximum contact were generated using the 3D footprint visualization feature of Catwalk XT 8.1. Digit prints for each pawprint image were then counted in a blinded fashion. Measurements of static and dynamic parameters of pawprints and gaits were then exported into Microsoft Excel and statistical analysis conducted using SigmaStat software.

Calculations of Percent Recoveries for Catwalk Locomotor Performance Scores.

To estimate percent recoveries for gridwalk and Catwalk results, average scores for each experimental group measured at pre-injury, pre-treatment, and 5 weeks post-injury were used. From these averages, percent recovery (% Recovery) was calculated as follows:

$$\% \text{ Recovery} = \frac{X_{Post\,Inj} - X_{Pre\,Tx}}{X_{Pre\,Inj} - X_{Pre\,Tx}} \times 100\%,$$

$X_{Pre\,Inj}$=Average score for behavioral parameter before injury
$X_{Pre\,Tx}$=Average score for parameter just prior to treatment
$X_{Post\,Inj}$=Average score for parameter at specified time following injury Anterograde Biotinylated Dextran Amine (BDA) Tracing of the Forelimb Corticospinal Tract (CST)

Two weeks prior to euthanasia, all animal groups were anesthesized and placed into a stereotaxic instrument (Kopf) for forelimb CST tracing. Following exposure of the skull, four burr holes were made using a surgical drill and 4 pressure injections of 0.5 µl of a 10% solution of biotinylated dextrane amine (BDA 10,000 MW, Invitrogen, Carlsbad, Calif., USA) in PBS were made into the left forelimb sensorimotor cortex (stereotaxic coordinates: 1.0 and 2.0 mm anterior to bregma, 2.5 and 3.5 mm lateral to bregma, and 1.6 mm depth from cortical surface).

Injections were made through a finely-pulled glass capillary that remained in position for 2 min following delivery. Following BDA injections, animals were sutured and allowed to recover. Visualization of BDA labeled axons within histological cross sections of spinal cord tissues was conducted with standard immuno-histochemistry procedures (see Davies J. E., et al. Astrocytes derived from glial restricted precursors promote spinal cord repair Journal of Biology 5:7 (2006). Spinal cord sections were viewed and imaged on a Zeiss Observer Z1 micro-scope using AxioVision software.

Density Analyses of CST/BDA and Synapsin-1 in Spinal Gray Matter

ImageJ software was used to threshold and to measure the densities of BDA-labelled CST axons and synapsin-1. CST densities were measured in the dorsal horn gray matter at the C5 spinal level. Every sixth section in a series was measured through approximately 400 μm of tissue. Synapsin-1 densities were measured in a similar manner below the injury cavity (C6) in the ventral horns around neuron pools of lamina IX.

Cat Walk Analysis Shows Intrathecal Infusion of Decorin Promotes Robust Recovery of Locomotor Functional and Digit Use after Traumatic Spinal Cord Injury.

In addition to gridwalk analysis, recovery of locomotor function of experimental groups was also assessed using CatWalk gait analyses at 5 weeks post injury/3 weeks post treatment. As previously reported by Gensel, et al. (Behavior and histological characterization of unilateral cervical spinal cord contusion injury in rats. *J. Neurotrauma* 23, 36-54 (2006)) following a unilateral cervical contusion, there was no significant changes in the dynamic parameters for limbs on the ipsilateral side following injury, such as changes in print positions, base of support, stride length, or footfall pattern. Statistically significant changes compared to pre-injury values were however found at the pre-treatment/12 days post-injury for a variety of paw specific parameters such as for print area, print intensity, print area at maximum contact, maximum contact relative to stance, and maximum intensity at maximum contact (FIGS. 4A-4H).

Mean Paw Print Area.

Print area is defined as the surface area of a complete paw print over the entire time the paw was in contact with the glass plate, comparable to ink pad method of determining print area (F. P. Hamers, et al. CatWalk-assisted gait analysis in the assessment of spinal cord injury. *J. Neurotrauma* 23, 537-548 (2006)). Analysis of paw print areas for all experimental animals revealed comparable pre-injury baseline values for mean print areas for right (ipsilateral) forelimbs and hindlimbs for all individual rats prior to injury and prior to treatment. Unilateral contusion injuries at the C4/C5 spinal level resulted in significantly reduced mean print areas for fore and hindlimbs ipsilateral to sites of injury for all experimental rats. Decorin treatment of spinal cord injured rats at 12 days post injury resulted in statistically significant recovery in mean print area for both fore and hind ipsilateral limbs at five weeks post-injury compared to saline and catheter alone untreated spinal cord injured rats.

Figure 4A:
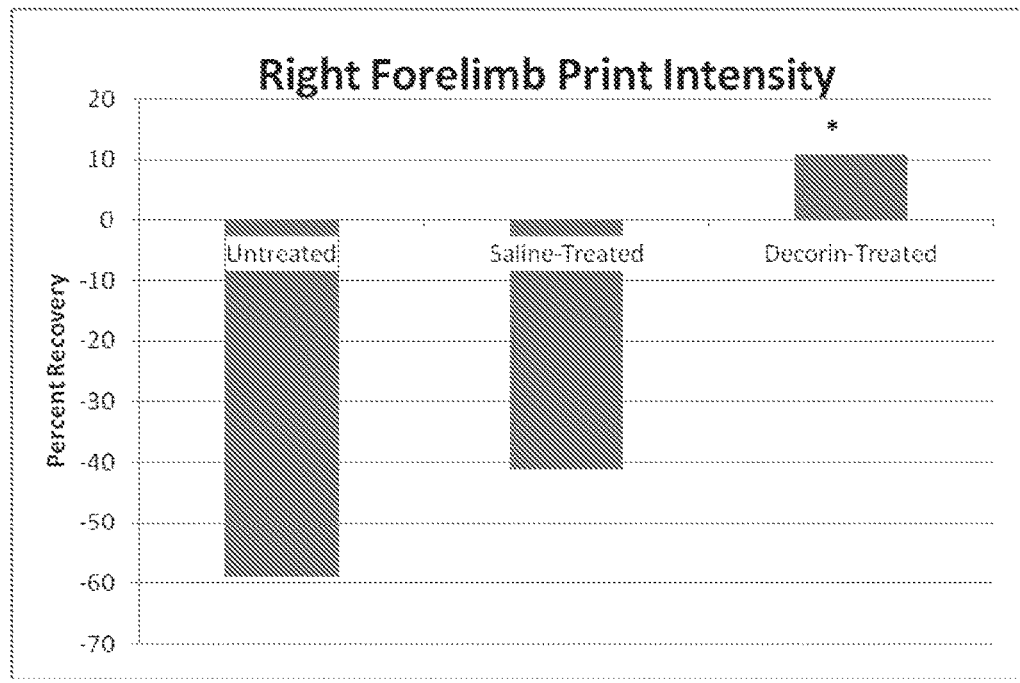
FIGS. 4A-4H CatWalk Analysis. In addition to recovery observed on Grid Walk/horizontal ladder testing, decorin-treated rats exhibited robust behavioral recovery of three forelimb and five hindlimb static parameters following delayed treatment of spinal cord contusion at 5 weeks post-injury. RF: Right forepaw; RH: Right Hindpaw.
Figure 4B:
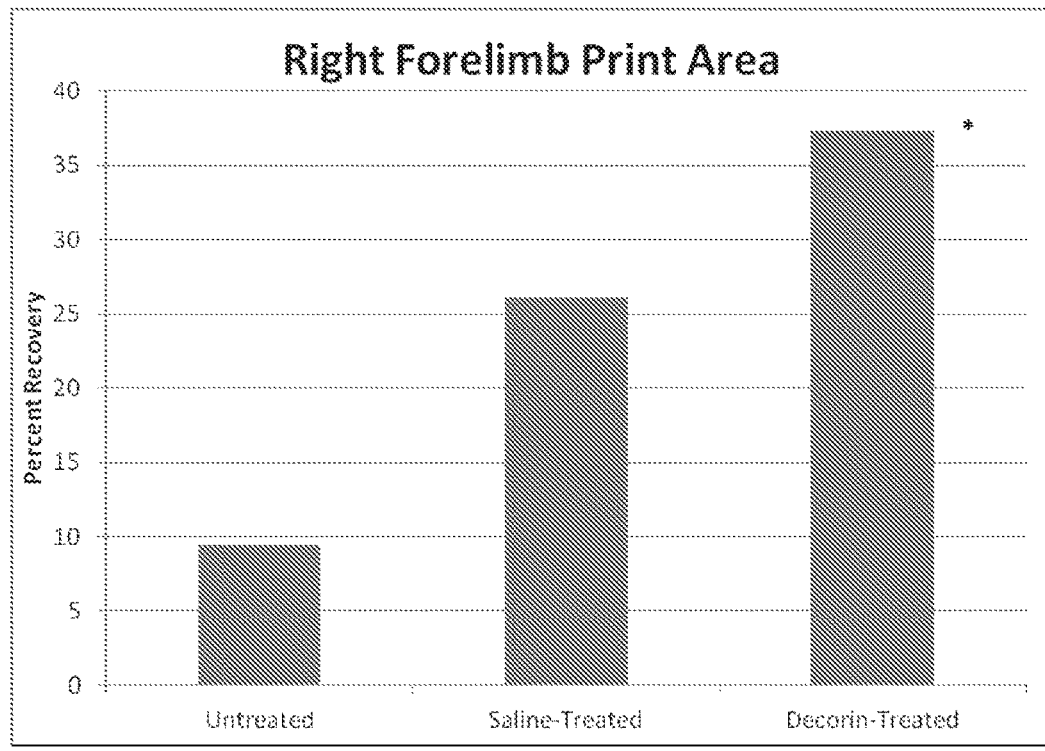
Figure 4C:
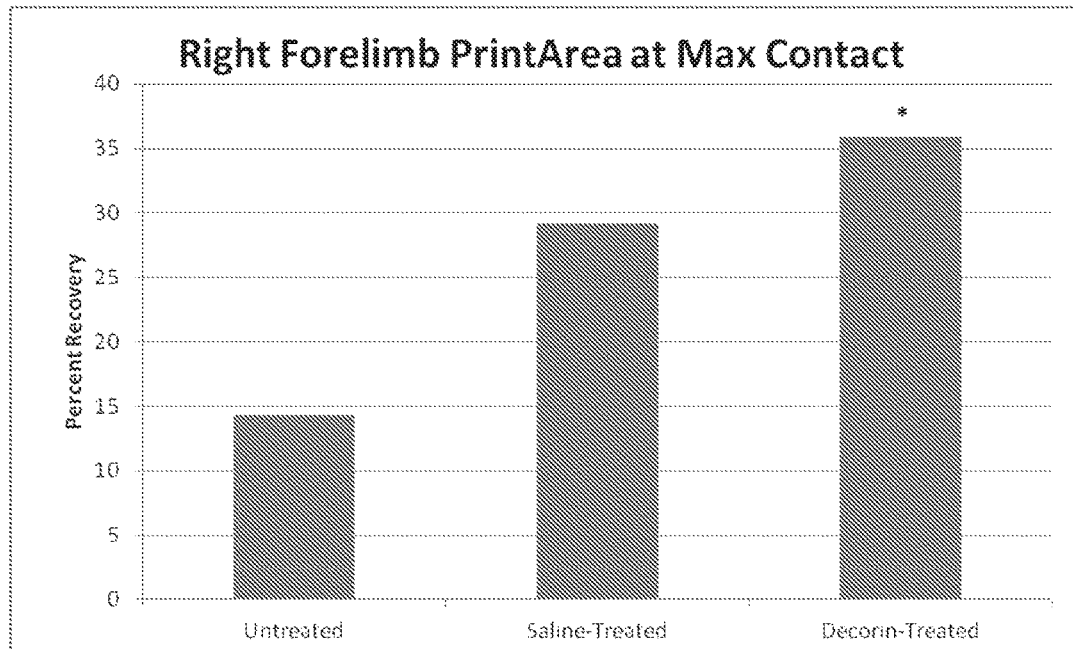
Figure 4D:
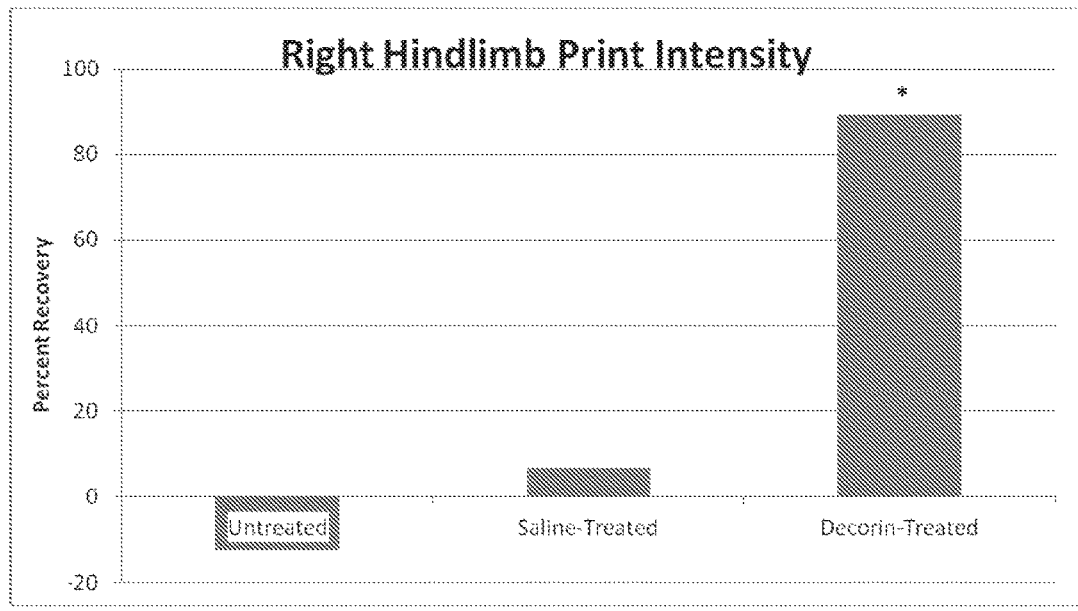
Figure 4E:
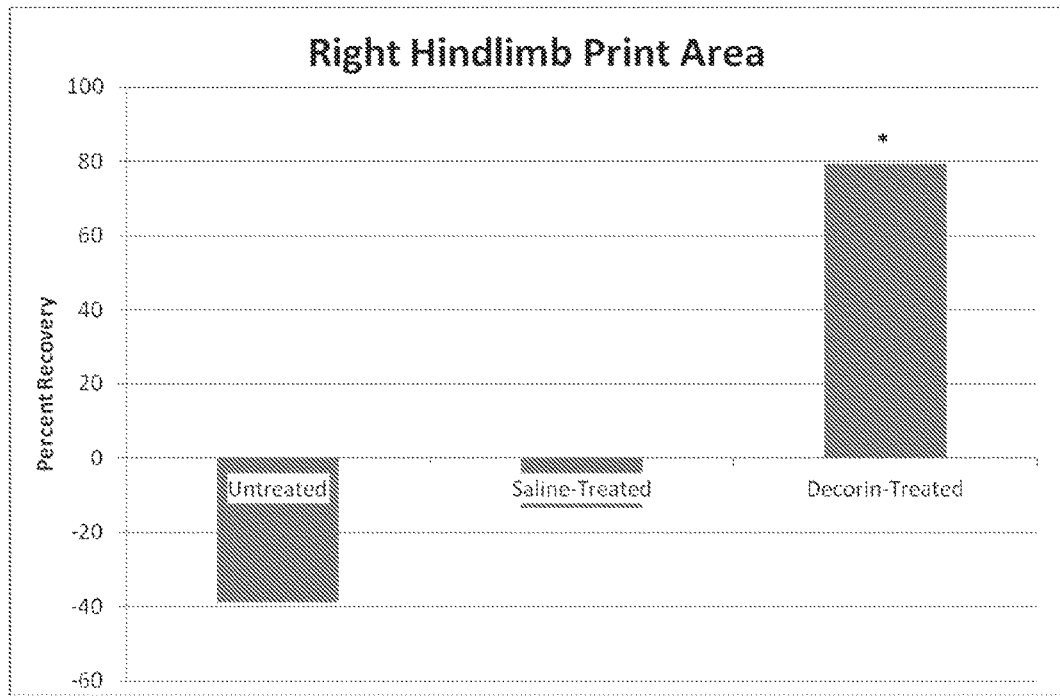

Percentage increases in recovery of mean paw print area were determined by subtracting pre-treatment mean print area values from baseline pre-injury values and expressing increases as a percentage of the difference. Compared to pre-treatment values, decorin treated SCI rats showed a 37.36% recovery in right forelimb mean print area (FIG. 4B) and a 79.23% recovery in the right hindlimb mean print area (FIG. 4E) i.e. a near return to baseline pre-injury levels. Animals treated with saline showed a relatively modest 26.08% recovery in forelimb mean print area but a further 13.3% loss in hindlimb mean print area at five weeks post injury (FIGS. 4B and 4E) compared to pre-treatment values. Spinal cord injured rats that received a catheter and no infusion exhibited a 9.45% recovery degree of recovery five weeks post injury in forelimb mean print area and a precipitous 38.67% loss in hindlimb print area i.e. a further loss of paw function compared to the 12 day post-injury pre-treatment time point (FIGS. 4B and 4E).

Print Area at Maximum Contact.

Figure 4F:
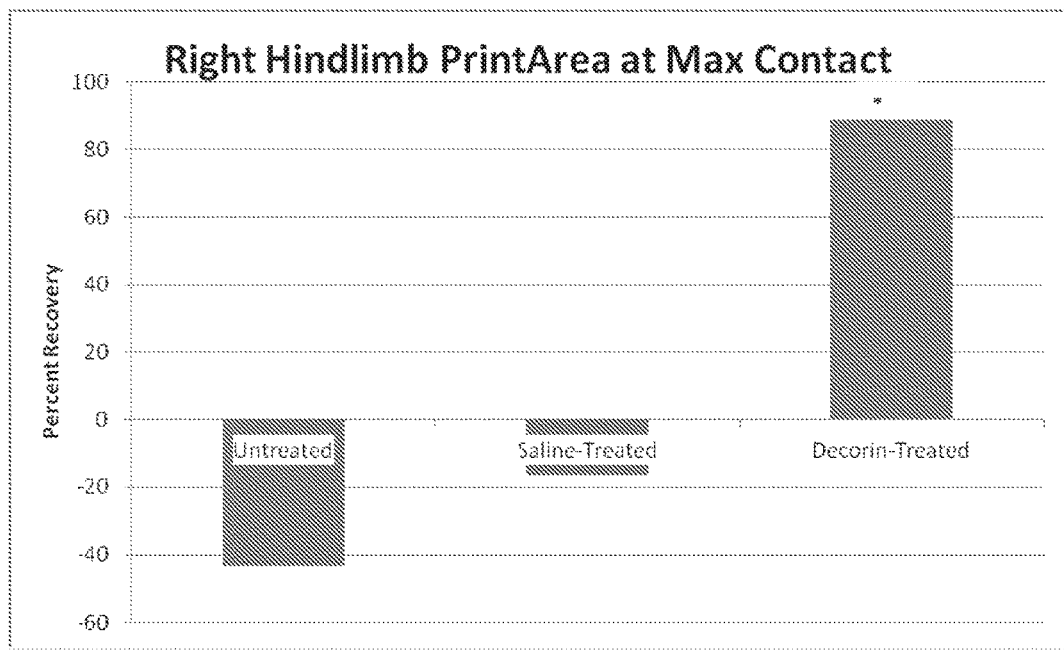
Figure 4G:
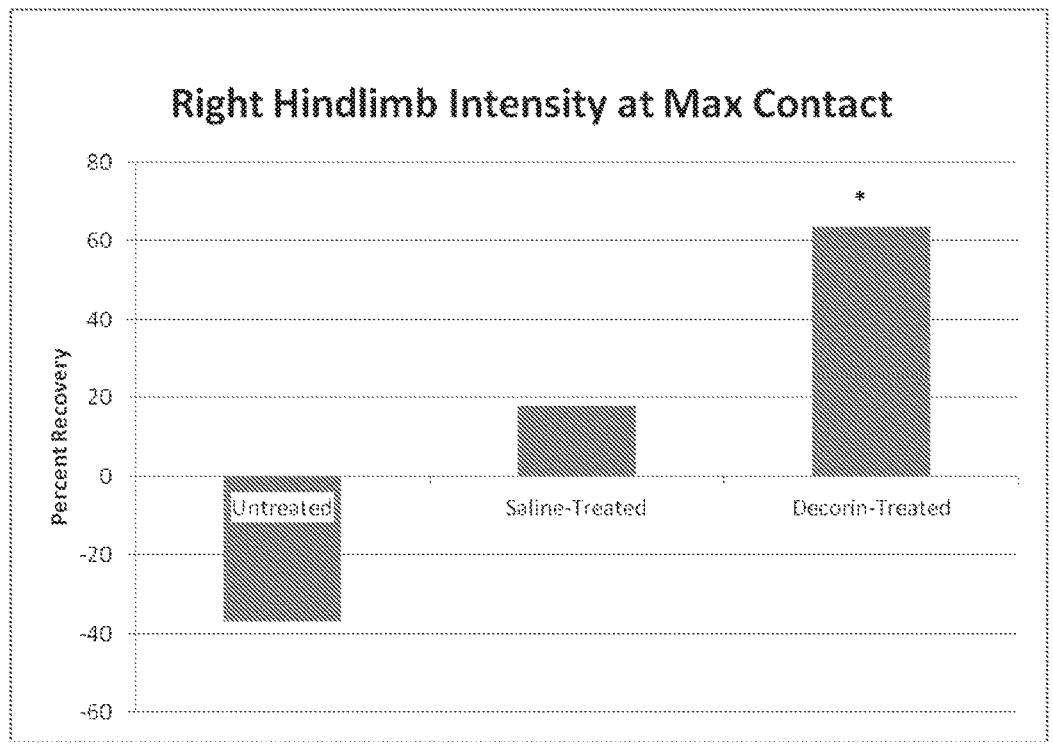

During locomotion, each paw generates a paw print area of maximum contact that occurs when the braking phase progresses into the propulsion phase of the paw's contact with the glass runway (Noldus Catwalk XT 8.1 users manual: (F. P. Hamers, et al. CatWalk-assisted gait analysis in the assessment of spinal cord injury. *J. Neurotrauma* 23, 537-548 (2006))). Each treatment group had pre-injury baseline values for print area at max contact for both ipsilateral fore and hindlimbs that were not statistically different from each other. At the 12 day post injury/pre-treatment time point, all treatment groups exhibited significant reductions in ipsilateral right forelimb and hindlimb print areas at maximum contact compared to baseline values. At 5 weeks post injury, decorin treated SCI rats exhibited significant recovery in the mean max contact area of the ipsilateral right fore and hindlimbs with maximum contact print areas for ipsilateral fore and hindlimbs reaching 35.92% and 88.82% recoveries respectively. At 5 weeks post injury, animals treated with saline however exhibited a relatively small 29.15% recovery in the mean max contact area of the right forelimb, and a 16.49% loss in the right hindlimb mean max contact area. Untreated control SCI animals showed an even smaller 14.34% recovery in the right forelimb mean max contact area compared to saline treated rats, and an even greater 43.35% loss of mean max contact area compared to pre-treatment values at 5 weeks post injury/3 weeks post-treatment (FIGS. 4C and 4F).

Mean Print Intensity.

Print intensity values are directly proportional to the pressure a paw exerts when it is in contact with the glass plate (F. P. Hamers, et al. CatWalk-assisted gait analysis in the assessment of spinal cord injury. *J. Neurotrauma* 23, 537-548 (2006)). SCI resulted in significant, consistent deficits in the mean intensity of the prints of the right forelimbs and hindlimbs across treatment groups. At 5 weeks post injury decorin treated animals exhibited a statistically significant 10.84% recovery in the mean print intensity values of the right forelimb, and an 89.28% recovery in the mean print intensity of the right hindlimb. Saline treated animals however exhibited a 41.16% loss of mean print intensity in the right forelimb and a 6.53% recovery in the mean print intensity of the right hindlimb. The untreated SCI controls exhibited a 58.87% loss of mean print intensity in the right forelimb and a 12.48% loss of the mean print intensity in the right hindlimb (FIGS. 4A and 4D).

Maximum Contact at Percentage of Stance.

This parameter as defined herein is being the period of time during which the paw is in contact with the glass runway (referred to as the "stance") at the point of maximum contact that divides the braking phase from the propulsion phase (otherwise known as max contact at %: Noldus manual). While each paw is used for both braking and propulsion, forepaws and hindpaws are utilized differently during each stance. Forelimbs are predominantly used for braking, while hindlimbs are mainly used for propulsion (Webb, A. A., et al. Compensatory locomotor adjustments of rats with cervical or thoracic spinal cord hemisections, *J. Neurotrauma* 19, 239-256 (2002); Webb, A. A., et al. Unilateral dorsal column and rubrospinal tract injuries affect overground locomotion in the unrestrained rat, *Eur. J. Neurosci.* 18, 412-422 (2003)). Thus, hindlimbs have a greater percentage of the stance (duration of glass contact) devoted to propulsion, and therefore the print area reaches maximum contact earlier in the stance. CatWalk measures this parameter as being the percentage of the stance when the hindlimb reaches maximum contact. Hence, prior to injury, hindlimbs reach maximum contact at a lower percentage of the stance compared to the forelimbs, because of their role in propulsion during locomotion.

Figure 4H:
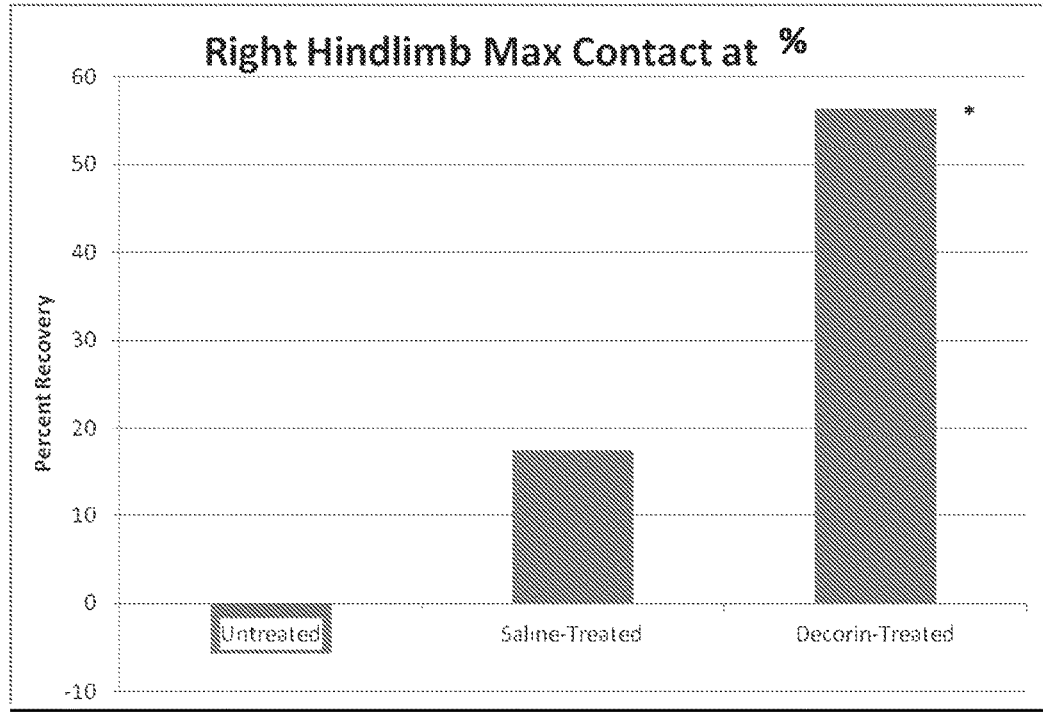

Our cervical contusion injury model resulted in a functional deficit in which the right hindlimb reached maximum contact at a significantly greater percentage of the stance (Max Contact at %) compared to the pre-injury baseline values for all animals. At five weeks post-injury, animals treated with decorin showed a significant decrease in max contact at % in the right hindlimb, corresponding to a 56.38% recovery of propulsion by this limb (FIG. 4H). Saline treated animals showed a minimal decrease in max contact at % (a 17.46% improvement), while untreated SCI controls continued to show a loss of function at five weeks post-injury (a 5.52% loss of function). Thus, treatment with decorin promoted a return towards a normal division of braking versus propulsion in hindlimb usage on the injured side of the animal, ultimately allowing for improved propulsion by the hindlimb during locomotion (FIG. 4H). [Note the title for FIG. 4H should read "Right Hindlimb Max Contact at %" and NOT "Right Hindlimb Max Contact at Mean"] Please correct this as you have the Excel files.

Max Contact Max Intensity.

The maximum intensity at the point of max contact is a measure of pressure and weight support exerted on the glass plate during the boundary of the braking and propulsion phases (Noldus Catwalk manual: (F. P. Hamers, et al. CatWalk-assisted gait analysis in the assessment of spinal cord injury. *J. Neurotrauma* 23, 537-548 (2006))). Our cervical contusion injury model caused a statistically significant reduction in this parameter compared to baseline values, indicative of dysfunction during the transition between the braking and propulsion phases. SCI rats treated with decorin showed a 63.51% recovery in this parameter in the right hindlimb five weeks post-injury, while saline treated animals exhibited a much smaller recovery of 17.81% and untreated controls showed a greater loss of 37.02% five weeks post-injury (FIG. 4G.

Digits at Maximum Contact

Hamers, et al. (CatWalk-assisted gait analysis in the assessment of spinal cord injury. *J. Neurotrauma* 23, 537-548 (2006)) previously showed that at the point of maximum contact, nearly all of the paw digits will be in contact with the glass plate for the hindpaws of normal uninjured rats. Our study confirmed this, and also showed that when the forepaw reaches maximum contact with the glass plate in uninjured rats, all of the digits (3.89±0.04 out of a possible 4 digits) make contact with the glass at this point as well. For the hindpaw in our study, uninjured animals showed an average of 3.75±0.11 out of 5 digits at maximum contact (Table 2). Our cervical contusion injury model resulted in a significant reduction in the average number of digit prints at maximum contact, in both the forepaws (1.95±0.12 digits) and the hindpaws (1.26±0.14 digits) ipsilateral to the injury at the 12 day post-injury/pre-treatment time point. SCI rats treated with decorin showed a significant recovery, with an average of 3.76±0.58 forepaw digit prints at 5 weeks post-injury, and 3.88±0.69 digit prints for the hindpaw. Saline treated rats showed a smaller recovery in the number of digit prints at maximum contact, with 2.58±0.47 forepaw digit prints and 1.37±0.78 digit prints for the hindpaw. Untreated controls showed even fewer digit prints at maximum contact, with averages of 2.19±0.60 in the forepaws, and 0.96±0.68 in the hindpaws.

As shown in Table 2, the CatWalk analysis showed intrathecal infusion of decorin promoted recovery of paw digit use in spinal cord injured rats. Decorin-treated spinal cord injured rats displayed paw prints at maximum contact with digit contact numbers remarkably similar to pre-injury prints as opposed to untreated spinal cord injured control rats that showed no recovery of digit use at 5 weeks post-spinal cord injury compared to pre-treatment scores.

TABLE 2

CatWalk Analysis

| | Untreated | Decorin Treated |
|---|---|---|
| Right Forepaw digit use (4 max) | 2.2 +/− 1.3 SD | 3.8 +/− 0.6 SD |
| Right Hindpaw digit use (5 max) | 1.0 +/− 1.5 SD | 3.9 +/− 1.4 SD |

Example 3

This example illustrates the effect of decorin administration in accordance with the present invention at varying time points (time=0, 12 days, 1 month) after injury on performance of spinal cord injured rats in a GridWalk analysis.

Figure 5:
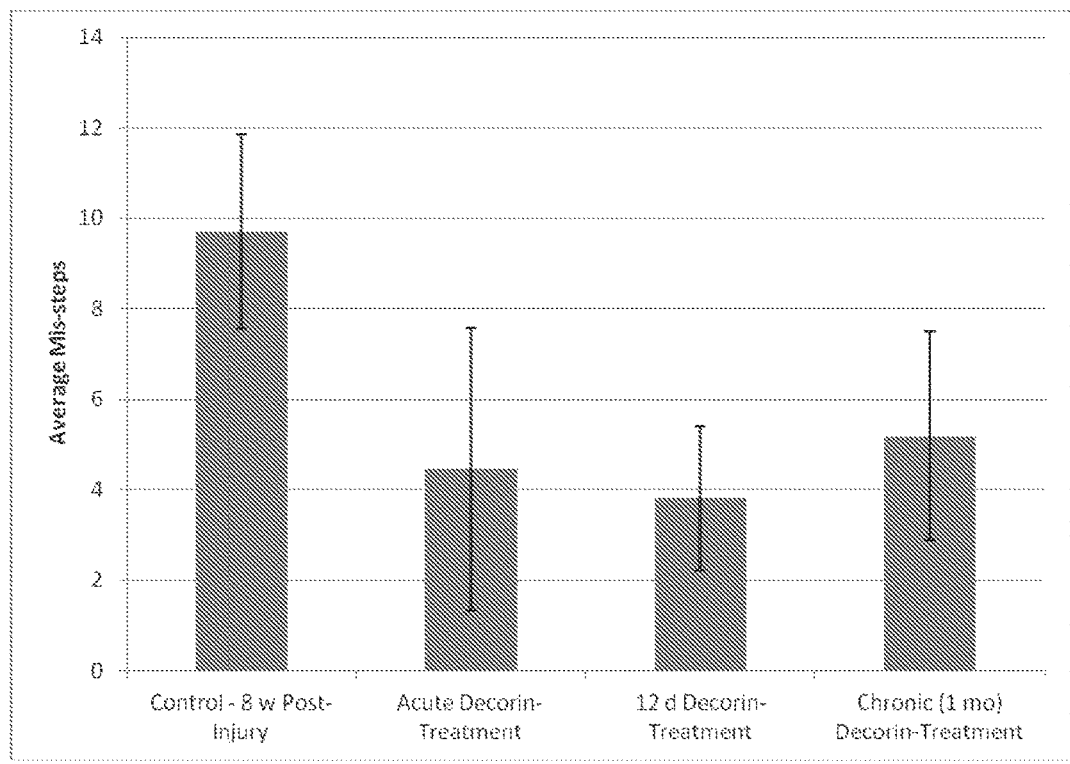
FIG. 5 GridWalk/Horizontal Ladder performance analysis. The graph show GridWalk/Horizontal Ladder performance scores (mis-steps) at 8 weeks post-injury for cervical contusion spinal cord injured rats treated with intrathecal decorin infusion commencing at: Acute (immediately after injury); 12 days (12 d) and 1 month (1 mo) chronic time points after injury.

The benefits of intrathecal infusion of decorin to the cisterna magna of adult rats with unilateral contusion injuries at the C4/C5 cervical spinal levels was analyzed. This analysis started either immediately after injury or 1 month after injury using comparable animal numbers per experimental groups and identical infusion, surgical and Grid-Walk/Horizontal Ladder behavior testing protocol as described for the results obtained of decorin infusion at 12 days post spinal cord injury. As shown in FIG. 5 there were robust reductions in numbers of mis-steps for rats crossing the Horizontal Ladder for all decorin treated rats compared to untreated control spinal cord injured rats that received a cannula alone to the cistern magna but no decorin infusion. The performance scores shown in FIG. 5 represent the performance scores (mis-steps) at 8 weeks post-injury for cervical contusion spinal cord injured rats treated with intrathecal decorin infusion commencing at: Acute (immediately after injury), 12 days (12 d) and 1 month (1 mo) chronic time points after injury.

Example 4

This example illustrates the effect of decorin treatment on increases in CST collateral density within gray matter adjacent to and below sites of injury.

Figure 6:
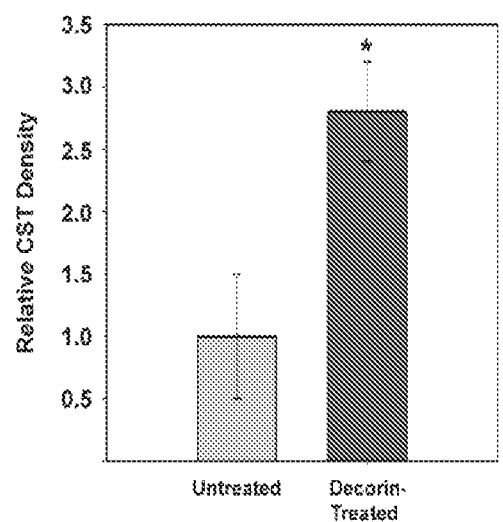
FIG. 6. Decorin promotes sprouting of motor control spinal circuits. Spinal cords treated with decorin at 12 day post-SCI display increased cortico-spinal tract (CST) axon densities in dorsal horn gray matter caudal to sites of injury compared to untreated injured spinal cords at 9 weeks post-treatment. Quantitative analysis demonstrated a 2.8-fold greater CST axon density in the dorsal horn gray matter within medial laminae I-VI in decorin-treated spinal cords versus untreated controls. Asterisk indicates significant difference (p<0.05) as determined using one-way ANOVA statistical.

Previous studies have shown significant deficits in forelimb function after unilateral cervical contusion injury at the C4-C5 level despite sparing the dorsal column CST white matter, and collateral sprouting of the CST at the cervical level has been shown to correlate with locomotor recovery after spinal cord injury (Schucht, P., et al. Anatomical correlates of locomotor recovery following dorsal and ventral lesions of the rat spinal cord, *Exp. Neurol.* 176, 143-153 (2002)). This example evaluates the ability of intra-thecal infusion of decorin to promote CST axon collateral plasticity within surviving gray matter caudal to sites of injury. In decorin-treated and untreated SCI rats, biotinylated dextran amine (BDA) was injected into the forelimb area of the left hemisphere sensorimotor cortex to trace the axons and collaterals of layer V upper motor neurons within the right side CST of the cervical spinal cord. Serial section histological analysis of gray matter of decorin versus untreated spinal cords, above, adjacent and below sites of injury revealed the most significant changes in BDA+CST collateral density were within laminae 1-5 dorso-medial gray matter (FIG. 6), a CST terminal field known to support sensorimotor function. The collaterals of forelimb CST axons showed extensive ramification and arborization within laminae 1-5 dorso-medial gray matter caudal to sites of injury when compared to untreated controls. Quantitative serial section analysis demonstrated that decorin-treatment promoted a 2.8 fold increase in density of BDA-labeled CST axons within laminae 1-5 dorso-medial gray matter versus that observed in untreated spinal cords (FIG. 6).

Example 5

This example illustrates the ability of intrathecal infusion of decorin to promote synaptic plasticity within ventral gray matter motor neuron pools.

Figure 7:
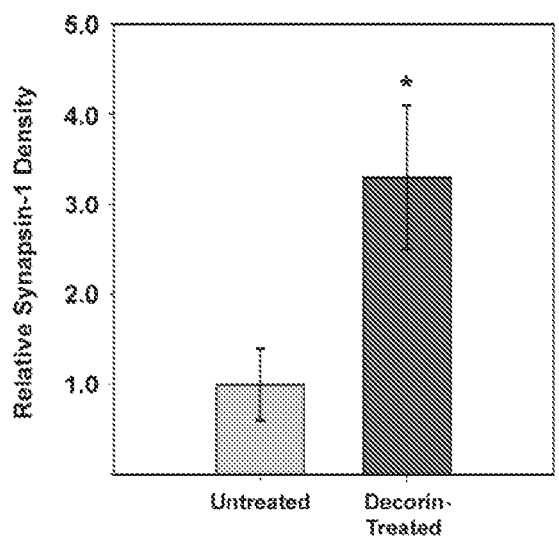
FIG. 7 Decorin promotes synaptogenesis in the injured central nervous system. Spinal cords treated with decorin displayed greater immuno-density for the pre-synaptic vesicle protein synapsin-1 compared to untreated controls in ventral horn gray matter at the C6 spinal level caudal to the injury site. Graph of density analysis showing an average 3.2 fold increase in levels of Synapsin-1 immuno-densities for decorin-treated spinal cords vs. untreated controls. (*) indicates significant difference (p<0.05) as determined using one-way ANOVA statistical comparison.

The synaptic plasticity within gray matter of injured decorin-treated and untreated controls spinal cords was analyzed, focusing on synapsin-1, a pre-synaptic protein found within active synapses and known to play roles in synaptic maturation and long-term synaptic maintenance and transmission (Lu, B. Expression of synapsin I correlates with maturation of the neuromuscular synapse. *Neuroscience* 74, 1087-1097 (1996); Thiel. G. Synapsin I, synapsin II, and synaptophysin: marker proteins of synaptic vesicles, *Brain Pathol.* 3, 87-95 (1993); Gulino, R., et al. Synaptic plasticity modulates the spontaneous recovery of locomotion after spinal cord hemisection, *Neurosci. Res.* 57, 148-156 (2007); Koelsch, A., et al. Transgene-mediated GDNF expression enhances synaptic connectivity and GABA transmission to improve functional outcome after spinal cord contusion. *J Neurochem.* 113, 143-152 (2010); Mundy, W. R., et al. Protein biomarkers associated with growth and synaptogenesis in a cell culture model of neuronal development, *Toxicology* 249, 220-229 (2008); De, C. P., et al. Synapsin I (Protein I), a nerve terminal-specific phosphoprotein. II. Its specific association with synaptic vesicles demonstrated by immunocytochemistry in agarose-embedded synaptosomes, *J Cell Biol.* 96, 1355-1373 (1983)). Synapsin-1 immuno-density was elevated within ventral gray matter below the level of injury at the C6 spinal level for lamina IX motor neuron pools that control forelimb movement. As shown in FIG. 7, decorin-treated spinal cords displayed striking increases in synapsin-1 immuno-density within ventral gray matter when compared to untreated controls. In decorin-treated spinal cords, increases levels of synapsin-1 puncta were observed on both neuronal cell bodies and dendrites, with little or no evidence of synapsin-1 directly associated with GFAP+astrocyte cell bodies or processes. Serial section quantitative analysis revealed a 3.2 fold increase in Synapsin-1 immuno-density in C6 lamina IX motor neuron pools in decorin-treated cords compared to untreated control cords (FIG. 7).

While various embodiments of the present invention have been described in detail, it is apparent that modifications and adaptations of those embodiments will occur to those skilled in the art. It is to be expressly understood, however, that such modifications and adaptations are within the scope of the present invention, as set forth in the following exemplary claims.

The invention claimed is:

1. A method of treating cerebral palsy resulting from brain injury in a patient, comprising administering decorin or a fragment thereof comprising a decorin core protein to the intrathecal cavity of the patient, to thereby treat the cerebral palsy resulting from brain injury.

2. The method of claim 1, wherein the step of administering comprises administering decorin to a portion of the intrathecal cavity selected from the group consisting of cisterna cerebellomedullaris (cisterna magna), the intrathecal cavity at the cervical, thoracic, lumbar and sacral spinal cord levels, and infusion to the cerebral spinal fluid (CSF) surrounding the corda equina.

3. The method of claim 1, wherein the step of administering comprises administering a bolus of decorin or the fragment thereof to the patient.

4. The method of claim 3, further comprising continuous delivery of decorin or the fragment thereof to the patient.

5. The method of claim 1, wherein the patient is a human.

6. The method of claim 1, wherein the decorin fragment is human decorin core protein.

7. The method of claim 1, wherein the decorin is human decorin, or a fragment thereof comprising human decorin core protein.

8. The method of claim 1, wherein the decorin or fragment thereof is chemically modified.

9. The method of claim 1, wherein the method further comprises an additional treatment for cerebral palsy.

10. The method of claim 9, wherein the additional treatment for treating cerebral palsy comprises administering anti-inflammatory agents, cell transplant based therapies, temperature reducing agents, immobilization, cell infusion based therapies, implantation of biomaterials, intrathecal infusion of a small leucine repeat protein (SLRP) releasing nano-particles, exercise therapies, functional electrical stimulation based rehabilitative therapies, surgical interventions, or clinically induced hypothermia based CNS therapies.

\* \* \* \* \*